(12) United States Patent
Tromberg et al.

(10) Patent No.: US 11,160,470 B2
(45) Date of Patent: Nov. 2, 2021

(54) MOTION TRACKING APPARATUS AND METHOD

(71) Applicant: The Regents of the University of California, Oakland, CA (US)

(72) Inventors: Bruce J. Tromberg, Irvine, CA (US); Kyle Cutler, Irvine, CA (US); Chris Van Wagenen, Irvine, CA (US); Seung-ha Lee, Irvine, CA (US); Thomas O'Sullivan, Irvine, CA (US); Gopi Meenakshisundaram, Irvine, CA (US); Aditi Majumder, Irvine, CA (US); Albert Cerussi, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/169,426

(22) Filed: May 31, 2016

(65) Prior Publication Data

US 2016/0345858 A1 Dec. 1, 2016

Related U.S. Application Data

(60) Provisional application No. 62/169,447, filed on Jun. 1, 2015.

(51) Int. Cl.
*A61B 5/06* (2006.01)
*A61B 5/00* (2006.01)
*A61B 5/11* (2006.01)

(52) U.S. Cl.
CPC ............ *A61B 5/067* (2013.01); *A61B 5/0075* (2013.01); *A61B 5/062* (2013.01); *A61B 5/064* (2013.01); *A61B 5/065* (2013.01); *A61B 5/1128* (2013.01); *A61B 5/1127* (2013.01); *A61B 2560/0223* (2013.01); *A61B 2562/0219* (2013.01); *A61B 2562/0223* (2013.01)

(58) Field of Classification Search
CPC ................................ A61B 34/10; A61B 34/30
See application file for complete search history.

(56) References Cited

U.S. PATENT DOCUMENTS

| | | | |
|---|---|---|---|
| 8,244,332 B2 | 8/2012 | Azar et al. | |
| 8,712,504 B2 | 4/2014 | Godavarty et al. | |
| 9,375,147 B2* | 6/2016 | Courtney | A61B 5/0062 |
| 2007/0219450 A1* | 9/2007 | Azar | G01N 21/474 |
| | | | 600/476 |
| 2007/0293792 A1* | 12/2007 | Sliwa | A61B 5/11 |
| | | | 600/587 |

OTHER PUBLICATIONS

Cutler, Surface Motion Tracking Hardware for use in Reflectance-based Diffuse Optical Imaging, 2014, University of California, Irvine.

* cited by examiner

*Primary Examiner* — Michael J D Abreu
(74) *Attorney, Agent, or Firm* — Sean Senn

(57) ABSTRACT

In accordance with various embodiments herein, disclosed herein is an apparatus comprising an imaging probe-based device operably linked to an automated tracking system. Furthermore, in various embodiments, the apparatus may be used to track the position and movement of a handheld imaging probe, including with respect to a subject's 3D surface profile. In one embodiment, a device may be used to track the position and movement of a handheld imaging probe with respect to a subject's 3D surface profile, while simultaneously acquiring optical data.

11 Claims, 29 Drawing Sheets

Background Material

10cm

10x Absorbing inclusion

MOTION TRACKING APPARATUS AND METHOD

CROSS-REFERENCE TO RELATED APPLICATIONS

The present application claims the benefit of priority under 35 U.S.C. § 119(e) of provisional application Ser. No. 62/169,447 filed Jun. 1, 2015, the contents of which are hereby incorporated by reference.

GOVERNMENT RIGHTS

This invention was made with Government support under Grant Nos. CA142989 and EB015890, awarded by the National Institutes of Health. The Government has certain rights in this invention.

FIELD OF THE INVENTION

The present disclosure is in the field of medicine and spectroscopy, specifically medical imaging.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Medical imaging has played a significant role in the advancement of prevention, diagnosis, and treatment of disease. Many imaging modalities have become a part of the standard of care because of the valuable information they provide clinicians. Throughout a long history of technology development, different types of imaging have been created to address and collect specific types of information depending on the particular size scale. The field of medical imaging has techniques to look at tissues on several different levels of detail types of tissue. Blood vessels, for instance, can be examined with ultrasound to provide detail down to a few millimeters over a large area, while optical coherence tomography (OCT) can provide detail of a few microns but within a much smaller area. This illustrates the common trade-off between imaging area and resolution in medical imaging.

From diagnosing a disease with no visible symptoms to noninvasively monitoring the progress of a patient with extensive problems, imaging has been able to provide easier solutions to previously difficult situations. The use of imaging in diagnosis and prevention as well as treatment monitoring is similar. A patient or area of interest on a patient is measured with a particular modality, then the image or video is examined by a doctor who specializes in understanding the data type. In many cases the changes over time in a patient are of interest, so the patient is measured again at a later time. The changes in the data are examined in many ways depending on a modality but usually the same area is examined. This measurement structure can provide information on the progression of a chronic disease such as atherosclerosis or information on whether a treatment is working as intended such as radiation or chemotherapy of a tumor. In both cases the change in information or progression is of great interest to the clinician.

Diffuse Optical Spectroscopic Imaging (DOSI) is a medical imaging technique that combines the use of modulated and continuous-wave (CW) near infrared (NIR) light to measure the optical properties of tissue over a broad spectral range. However the current DOSI technique has limited spatial resolution and long measurement time. Thus, there remains a need in the art to improve both DOSI measurement procedures to enable faster measurement time and adjustable spatial resolution, as well as medical imaging techniques in general.

SUMMARY OF THE DISCLOSURE

In various embodiments, disclosed herein is an apparatus, comprising: an imaging probe-based device operably linked to an automated tracking system. In some embodiments, the imaging probe-based device is a handheld imaging probe. In some embodiments, the apparatus performs diffuse optical spectroscopy (DOS). In some embodiments, the automated tracking system tracks location with respect to a subject's 3D surface profile while simultaneously acquiring optical data. In some embodiments, the apparatus further comprising capability for intuitive visualization of imaging data by a user.

In other embodiments, the present invention provides an apparatus for tracking a 3D surface profile, comprising one or more motion tracking sensors integrated with an imaging probe, where the one or more motion tracking sensors captures a 3D surface profile. In one embodiment, the apparatus comprises a plurality of sensors. In one embodiment, the device is an electronic device. In one embodiment, the device is a handheld electronic device. In one embodiment, the apparatus tracks the subject's 3D surface profile. In one embodiment, the apparatus further acquires optical data.

Other embodiments include a method of visualizing a target, comprising providing an apparatus comprising an imaging probe-based device operably linked to an automated tracking system, and visualizing the target through the apparatus. In another embodiment, the apparatus performs noninvasive diffuse optical spectroscopy (DOS). In another embodiment, the apparatus comprises one or more motion tracking sensors integrated with an imaging probe.

In various embodiments, disclosed herein is an apparatus for tracking a 3D surface profile, comprising: one or more motion tracking sensors integrated with an imaging probe, wherein the one or more motion tracking sensors capture a 3D surface profile. In other embodiments, disclosed herein is an apparatus for tracking the position and movement of a handheld imaging probe with respect to a subject's 3D surface profile, wherein the system also simultaneously acquires optical data. In one embodiment, the apparatus further comprises visualization of imaging data. In one embodiment, a user of the apparatus can dynamically adjust the data collection field such as to collect higher spatial resolution data over a region of interest without having to separately record the additional sampling points. In one embodiment, the apparatus operates automatically or semi-automatically. In one embodiment, the automated tracking apparatus improves the usability of the device and reduces the complexity of DOS and other imaging probe-based techniques.

In various embodiments, disclosed herein is a position tracking apparatus, comprising: acquisition of a 3D surface profile over a DOS probe, and scanning the same; capturing the motion of the DOS probe while it is translated across the surface; a position calibration and data fusion scheme to co-register the two pieces of information; and an integrated probe with tracking electronics and optical fibers. In some embodiments, the acquisition of 3D surface profile comprises the steps of using Microsoft Kinect device and Kinect Fusion software. In other embodiments, the acquisition of the 3D surface profile further comprises the steps: using open source code from Point Cloud Library to apply the color image to the 3D mesh using the camera coordinates; and importing the textured 3D mesh into JMonkeyEngine for position tracking. In other embodiments, the motion of the DOS probe was captured using a system comprising three inertial motion sensors and one optical displacement sensor. In other embodiments, the inertial motion sensors comprises: an accelerometer, a magnetic compass, and a gyroscope, integrated onto a single printed circuit board. In other embodiments, the sensors are interfaced with an Arduino Due microcontroller to acquire the sensor data and transfer the data to a computer. In other embodiments, the inertial motion sensors were used with a modified implementation of an open source sensor fusion algorithm using a Directional Cosine Matrix (DCM) to represent changes in orientation of the imaging probe. In other embodiments, the optical displacement sensor is placed on the bottom of the imaging probe and wherein the sensor measures the displacement of the imaging probe on the skin surface. In other embodiments, the displacement, combined with orientation data from the DCM allows for the calculation of the relative motion along the measurement surface.

In various embodiments, disclosed herein is a motion tracking system, comprising a combined three dimensional (3D) scanned surface and embedded inertial/optical motion sensor. In some embodiments, the motion tracking system is used in combination with a fast CW DOSI system to decrease single point measurement speed. In some embodiments, the system is able to increase the spatial resolution of optical absorption measurements relative to a DOSI system. In some embodiments, the system is calibrated to quantify the repeatability of each sensor type, as well as the projection onto the 3D surface. In some embodiments, the motion tracking system further comprises one or more circuit, accelerometer, gyroscope, and magnetic compass. In some embodiments, the circuit is a combined ADNS-9800 optical mouse integrated circuit. In some embodiments, the accelerometer is ADXL345 accelerometer. In some embodiments, the gyroscope is ITG-3200 gyroscope. In some embodiments, the magnetic compass is HMC5883L magnetic compass. In some embodiments, the motion tracking system comprises a combined ADNS-9800 optical mouse integrated circuit, ADXL345 accelerometer, ITG-3200 gyroscope, and HMC5883L magnetic compass. In one embodiment, the sensors are connected to an arduino microcontroller which reads and outputs the data to a computer. In one embodiment, the 3D rotational information is calculated using a directional cosine matrix with input from the accelerometer, gyroscope, and magnetic compass. In one embodiment, the linear displacement on the surface is calculated from the digital signal processing chip embedded within the ADNS-9800 optical mouse integrated circuit. In one embodiment, the rotational and displacement data is combined with a 3D depth map taken from a microsoft Kinect using surface fiducial markers. In one embodiment, the motion tracking system further comprises software built using JMonkeyEngine and written in Java to record and visualize motion paths of the handheld probe on the surface.

In various embodiments, disclosed herein is a method of recording relative motion comprising information from handheld electronics, and a 3D scan, using software to record and visualize position and information about surface. In some embodiments, the information comprises medically relevant data.

In various embodiments, the present invention provides a device comprising one or more sensors that record relative motion information from handheld electronics, and a 3D scan using software to record and visualize position and information about surface.

In other embodiments, disclosed herein is a method of treating a disease, comprising: monitoring a disease by using an apparatus comprising an imaging probe-based device operably linked to an automated tracking system; and treating the disease. In some embodiments, the disease is cancer. In other embodiments, the disease is obesity.

Also disclosed herein, in various embodiments, is a method of diagnosing susceptibility to a disease in a subject, comprising monitoring a subject for one or more disease related conditions or markers using an apparatus comprising an imaging probe-based device operably linked to an automated tracking system, and diagnosing susceptibility to the disease based on the presence of the disease related conditions or marker. In some embodiments, the disease is cancer. In some embodiments, the one or more disease related conditions or markers is a tumor. In one embodiment, the disease is obesity.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION

Figure 1:
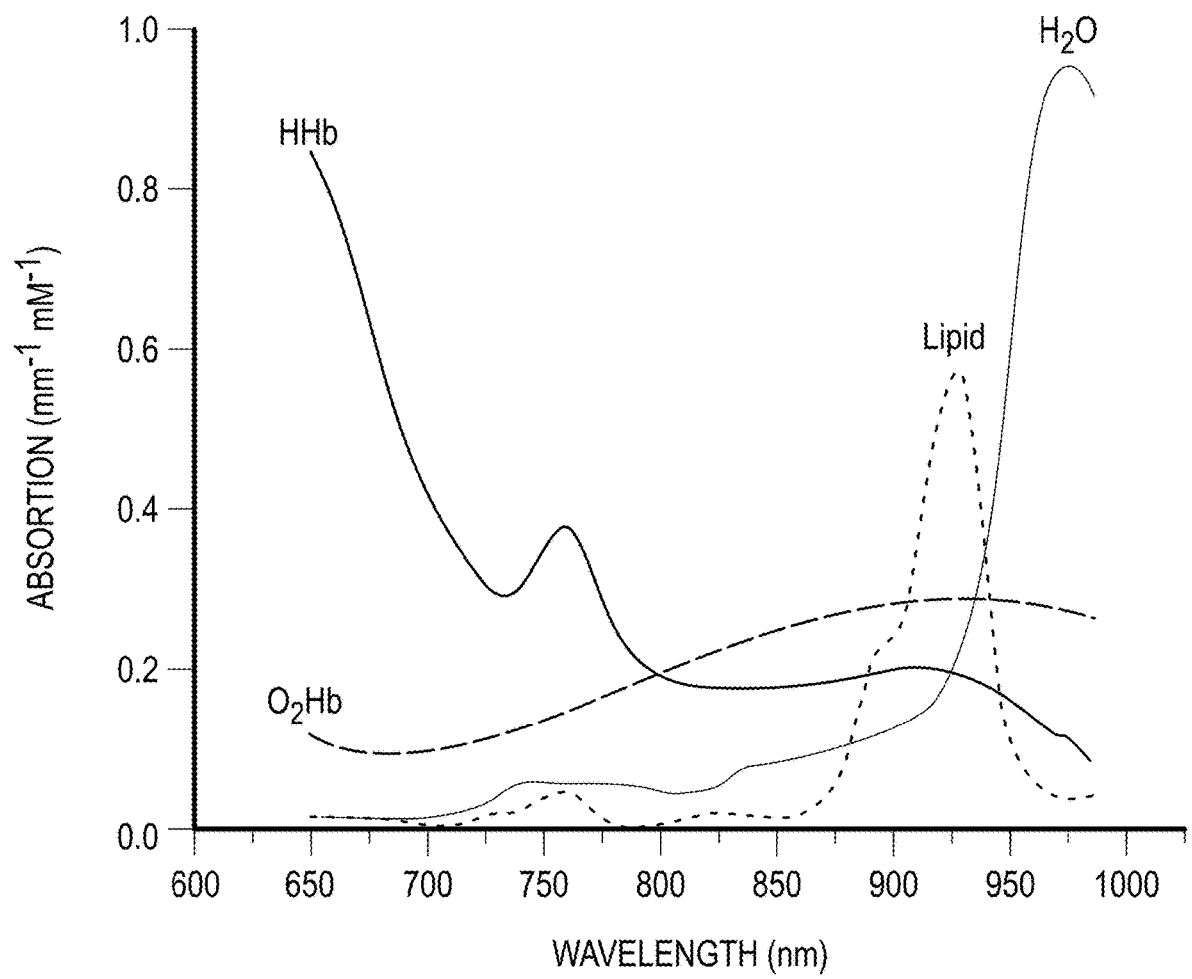
FIG. 1 depicts, in accordance with embodiments herein, DOSI absorption spectra.

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As described herein, in accordance with various embodiments disclosed herein, the inventors recorded the location of an imaging probe on the skin of a patient in order to display diffuse reflectance data in various spatial resolutions as well as in a patient specific 3D geometry. Microsoft Kinetic and open source software was used to acquire 3D scan of patient. Optical and electronic motion sensors were embedded in imaging probe to record motion. Laser Breast Scanning system was used to acquire reflectance data. Diffuse reflectance data was displayed using 3D surface and custom software. One dimensional recording provided displacement repeatability of 1.08-1.55%. Accuracy of unknown point estimation was between 4.49-23.20% depending on length of recorded path (15 mm-62 mm) and surface curvature. Various spatial resolution images of a patient's forearm were taken to show differences in optical contrast.

Currently, performing noninvasive diffuse optical spectroscopy (DOS) in thick tissues typically requires either a handheld probe manually scanned across a tissue of interest, or a large-format array of sources and detectors such as those employed in diffuse optical tomography. DOS instruments utilizing handheld probes are advantageous for their portability and relatively simple instrumentation, however, mapping the spatial distribution of DOS biomarkers over large areas requires a precise and oftentimes time-consuming data collection scheme. Furthermore, replicating imaging fields through multiple imaging sessions during longitudinal studies requires identifying and recording anatomical reference points. As further described herein, in accordance with various embodiments, the inventors have overcome many of these imaging limitations by developing a system which automatically tracks the position and movement of a handheld imaging probe with respect to the subject's 3D surface profile, while simultaneously acquiring optical data. Tracking location with respect to the subject's unique 3D surface profile allows for simple, intuitive visualization of imaging data. It enables the instrument operator, for example, to dynamically adjust the data collection field such as to collect higher spatial resolution data over a region of interest without having to separately record the additional sampling points. Overall, an automated tracking system can improve the usability and reduce the complexity of DOS and other imaging probe-based techniques.

In one embodiment, the present invention provides an apparatus, comprising: an imaging probe-based device operably linked to an automated tracking system. In another embodiment, the imaging probe-based device is a handheld imaging probe. In another embodiment, the apparatus performs diffuse optical spectroscopy (DOS). In another embodiment, the automated tracking system tracks location with respect to a subject's 3D surface profile while simultaneously acquiring optical data. In some embodiments, the apparatus further comprises capability for intuitive visualization of imaging data by a user.

In one embodiment, the present invention provides an apparatus for tracking a 3D surface profile, comprising one or more motion tracking sensors integrated with an imaging probe, where one or more motion tracking sensors capture a 3D surface profile. In one embodiment, the present invention provides an apparatus, comprising a sensor that records motion information from a device, where the apparatus tracks a subject's surface profile. In some embodiments, the apparatus comprises a plurality of sensors. In some embodiments, the device is an electronic device. In some embodiments, the device is a handheld electronic device. In one embodiment, the apparatus tracks the subject's 3D surface profile. In one embodiment, the apparatus further acquires optical data.

In accordance with various embodiments, the inventors developed an apparatus for tracking the position and movement of a handheld imaging probe with respect to a subject's 3D surface profile, where the system also simultaneously acquires optical data. In one embodiment, the apparatus further comprises visualization of imaging data. In another embodiment, a user of the apparatus can dynamically adjust the data collection field such as to collect higher spatial resolution data over a region of interest without having to separately record the additional sampling points. In some embodiments, the apparatus operates automatically or semi-automatically. In some embodiments, the automated tracking apparatus improves the usability of the device and reduces the complexity of DOS and other imaging probe-based techniques.

In one embodiment, the present invention provides a position tracking apparatus, comprising device for the acquisition of a 3D surface profile over a DOS probe, and scanning the same, capturing the motion of the DOS probe while it is translated across the surface, a position calibration and data fusion scheme to co-register the two pieces of information, and an integrated probe with tracking electronics and optical fibers. In one embodiment, the acquisition of 3D surface profile comprises the steps of using Microsoft Kinect device and Kinect Fusion software. In some embodiments, the acquisition of the 3D surface profile further comprises the steps: using open source code from Point Cloud Library to apply the color image to the 3D mesh using the camera coordinates; and importing the textured 3D mesh into JMonkeyEngine for position tracking. In some embodiments, the motion of the DOS probe was captured using a system comprising three inertial motion sensors and one optical displacement sensor. In one embodiment, the inertial motion sensors comprises: an accelerometer, a magnetic compass, and a gyroscope, integrated onto a single printed circuit board. In some embodiments, the sensors are interfaced with an Arduino Due microcontroller to acquire the sensor data and transfer the data to a computer. In some embodiments, the inertial motion sensors were used with a modified implementation of an open source sensor fusion algorithm using a Directional Cosine Matrix (DCM) to represent changes in orientation of the imaging probe. In some embodiments, the optical displacement sensor is placed on the bottom of the imaging probe and wherein the sensor measures the displacement of the imaging probe on the skin surface. In some embodiments, the displacement, combined with orientation data from the DCM allows for the calculation of the relative motion along the measurement surface.

As described herein, in accordance with various embodiments herein, the inventors recorded the unique 3D imaging surface of the patient and used a combination of optical and electronic sensors to record the physical location of the probe. In another embodiment, the translation is then quantified by measuring the relative displacement of the imaging probe compared to the surface using an optical sensor. In another embodiment, the rotation of the probe is measured with integrated motion unit that contains electronic inertial sensors. In another embodiment, these measurements combined with patient specific calibration allow the physical location to be determined.

As further described herein, specifically, the inventors addressed the need to record the physical location of a contact based imaging probe and subsequent measurement, specifically for using diffuse optical spectroscopic imaging. In one embodiment, a motion tracking system was developed using a combination of 3D scanned surface and embedded inertial/optical motion sensors. In another embodiment, the motion tracking system was used in combination with a fast CW DOSI system to decrease single point measurement speed. The combination system was able to increase the spatial resolution of optical absorption measurements as compared to previous generation DOSI system. In accordance with embodiments herein, the motion tracking system is calibrated to quantify the repeatability of each sensor type as well as the projection onto the 3D surface. As described herein, the displacement sensor had average percent errors of 1.203% and 1.552% over a flat surface at 50 mm, 100 mm respectively. The average percent error increased to 3.640% and 3.126% when repeated 50 mm and 100 mm displacement tests on human skin. The projection of motion paths on a flat optical phantom, exercise ball, and human lower leg was shown. The accuracy of unknown point estimation was shown with accuracy ranging from 21.9%-60%.

In one embodiment, the present invention provides a motion tracking system, comprising a combined 3D scanned surface and embedded inertial/optical motion sensor. In another embodiment, the motion tracking system is used in combination with a fast CW DOSI system to decrease single point measurement speed. In another embodiment, the system is able to increase the spatial resolution of optical absorption measurements relative to a DOSI system. In another embodiment, the system is calibrated to quantify the repeatability of each sensor type, as well as the projection onto the 3D surface.

As further disclosed herein, the inventors developed a device combining a ADNS-9800 optical mouse integrated circuit, ADXL345 accelerometer, ITG-3200 gyroscope, and HMC5883L magnetic compass. In another embodiment, the sensors are connected to an arduino microcontroller which reads and outputs the data to a PC. The 3D rotational information calculated using a directional cosine matrix with input from the accelerometer, gyroscope, and magnetic compass. In another embodiment, linear displacement on the surface is calculated from the digital signal processing chip embedded within the ADNS-9800 optical mouse integrated circuit. In accordance with embodiments herein, the combination allows the same types of sensors to be combined in other medical devices or handheld motion tracking systems to integrate the capabilities. In another embodiment, the rotational and displacement data is combined with a 3D depth map taken from a microsoft Kinect using surface fiducial markers. Custom software, built using JMonkey-Engine written in Java is used to record and visualize motion paths of the handheld probe on the surface. An advantage when compared to electromagnetic tracking system is the ability to use without interference from metal in the room with patient or tracking surface. As apparent to one of skill in the art, this is a fundamental problem with electromagnetic tracking systems that cast a homogenous magnetic field. An advantage when compared to optical tracking is the no direct line of sight is needed from camera onto surface or measurement probe, which allows for increased accuracy due to the device always being on surface.

In some embodiments, the motion tracking system disclosed herein further comprises one or more circuit, accelerometer, gyroscope, and magnetic compass. In one embodiment, the circuit is a combined ADNS-9800 optical mouse integrated circuit. In one embodiment, the accelerometer is ADXL345 accelerometer. In one embodiment, the gyroscope is ITG-3200 gyroscope. In one embodiment, the magnetic compass is HMC5883L magnetic compass. In one embodiment, the motion tracking system comprises a combined ADNS-9800 optical mouse integrated circuit, ADXL345 accelerometer, ITG-3200 gyroscope, and HMC5883L magnetic compass. In one embodiment, the sensors are connected to an arduino microcontroller which reads and outputs the data to a computer In one embodiment, the present invention provides a motion tracking system, wherein the 3D rotational information is calculated using a directional cosine matrix with input from the accelerometer, gyroscope, and magnetic compass. In another embodiment, the linear displacement on the surface is calculated from the digital signal processing chip embedded within the ADNS-9800 optical mouse integrated circuit. In another embodiment, the rotational and displacement data is combined with a 3D depth map taken from a microsoft Kinect using surface fiducial markers. In another embodiment, the system further comprises software built using JMonkeyEngine written in Java used to record and visualize motion paths of the handheld probe on the surface.

In one embodiment, the present invention provides a method of recording relative motion information from handheld electronics, combined with 3D scan, using software to record and visualize position and information about surface. In another embodiment, the information can be whatever measurement is taken, including medically relevant data. In another embodiment, the present invention provides for a device comprising one or more sensors that record relative motion information from handheld electronics, combined with 3D scan, using software to record and visualize position and information about surface.

In another embodiment, the present invention provides a method of treating a disease, comprising monitoring a disease by using an apparatus comprising an imaging probe-based device operably linked to an automated tracking system, and treating the disease. In some embodiments, the disease is cancer. In other embodiments, the disease is obesity.

In various embodiments, the present invention provides a method of prognosing a disease in a subject, comprising monitoring a subject for one or more disease related conditions or markers using an apparatus comprising an imaging probe-based device operably linked to an automated tracking system, and prognosing a severe form of the disease based on the presence of the disease related conditions or marker. In one embodiment, the disease is cancer. In other embodiments, the one or more disease related conditions or markers is a tumor. In one embodiment, the disease is obesity.

In various embodiments, disclosed herein is a method of diagnosing susceptibility to a disease in a subject, comprising monitoring a subject for one or more disease related conditions or markers using an apparatus comprising an imaging probe-based device operably linked to an automated tracking system, and diagnosing susceptibility to the disease in the subject based on the presence of the disease related conditions or marker. In one embodiment, the disease is cancer. In other embodiments, the one or more disease related conditions or markers is a tumor. In one embodiment, the disease is obesity.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Diffuse Optical Spectroscopy Background

Diffuse Optical Spectroscopic Imaging (DOSI) is a medical imaging technique under intense investigation that combines the use of modulated and continuous-wave (CW) near infrared (NIR) light to measure the optical properties (absorption and scattering) of tissue over a broad spectral range. Using the quantitative absorption and scattering properties along with molecular extinction coefficients, concentrations of abundant NIR chromophores can be determined within a measured area. In human tissues, the primary NIR chromophores include deoxygenated hemoglobin, oxygenated hemoglobin, water and lipid, which can provide functional information about healthy and diseased tissue states.

DOSI has shown significant potential for monitoring tumor response in breast cancer patients undergoing neoadjuvant chemotherapy. Neoadjuvant chemotherapy is administered to breast cancer patients before surgery in order to assess tumor chemosensitivity or to reduce the tumor size to enable a lesser surgery (e.g. a lumpectomy instead of a mastectomy). The current procedure for DOSI breast imaging first entails locating the tumor using ultrasound and identifying a region of interest around the tumor location. Since DOSI currently only samples data at a single point, a grid marking the desired measurement locations is inked over this region of interest using a transparent stamp. Each grid point is measured by placing a single-channel imaging probe at the specific marker. Each measurement point takes between 2-5 seconds, and the total number of points can range from a few dozen to a few hundred depending on the density and extend of the grid. The usual grid resolution has markers separated by 1 cm in each direction. The entire process of placing the imaging probe at each location, measuring that point, moving the probe to the next location, and scanning for all locations can take between 30-90 minutes depending on the quality of the data, the number of measured points and the absorption of the tissue.

While the current grid imaging protocols enable the ability to collect longitudinal patient data from the same location, its main drawback include limited spatial resolution and long measurement time. The spatial resolution cannot be dynamically adjusted because it needs to be determined before starting the measurement. The time of the measurement is related to the spatial resolution and individual point measurement time but also to the amount of time it takes to line up the probe with the individual markers.

In some embodiments provided herein, the DOSI measurement procedure is improved by creating a system that automatically records the location of DOSI measurement points by co-registering them with anatomical landmarks. In some embodiments, the system enables dynamically adjustable spatial resolution by allowing variable scanning speeds that allows for easily controllable ability to compare patient data between appointments density. The total measurement time is decreased because the time required to move and align the probe at each marker is greatly reduced or eliminated. In some embodiments, the physical location of the data on the tissue surface allows better comparisons between repeated measurements of a single patient at different time points.

Example 2

Diffuse Optical Imaging

Diffuse Optical Spectroscopic Imaging is a technique that combines the data from two different optical techniques to measure the concentrations of four primary chromophores. The two modalities are frequency domain photon migration (FDPM) and steady state broadband spectroscopy (SS). FDPM entails modulating the intensity of NIR laser diodes at hundreds of MHz using an RF source. The light travels through the tissue and when it leaves the tissue it is then detected by an avalanche photodiode on the surface. The phase and amplitude of the detected light are then compared to the original RF source to measure the change in both measures. This process is repeated for each of the laser diode sources (four in the current configuration) for modulation frequencies between 50-500 MHz. In the current configuration, one photodiode is used at a fixed offset for sequential measuring light from all four laser diodes. The frequency dependent amplitude and phase data are fit to a model of light propagation in tissue to quantify both absorption and scattering for each laser diode wavelength. The laser diodes are coupled to optical fibers that terminate at the imaging probe for surface illumination. The photodiode can either be inside the imaging probe itself or coupled using fiber optics.

The broadband light source is also fiber coupled to the imaging probe. After propagating through the tissue, light is collected via optical fiber and coupled to a spectrometer to measure a reflectance spectrum. The reflectance spectrum from the spectrometer does not take into account the decrease in signal due to scattering. The FDPM scattering values are fit to a power law to obtain a broadband scattering spectrum. The reflectance spectrum is then corrected using the broadband scatter spectrum to generate a broadband absorption spectrum. More information about using frequency modulated light can be found in a recent review paper (O'Sullivan, Cerussi et al. 2012). One advantage to using an imaging probe that directly contacts the surface of the skin is that the light penetrates deeper into the tissue than wide field based imaging techniques. The goal of recording the physical location of the probe during the measurement is to gain the high spatial resolution that is achieved by wide field imaging while maintaining the penetration depth that comes from contact based imaging.

Once the correct absorption spectrum is known, the concentration of four chromophores can be calculated using the average optical path length which is determined by the geometry of the sources and detectors as well as the optical properties of absorption and scatter. The farther apart the sources are from the detectors the less light will make it to the detector but the light that gets through will on average have travel farther through the tissue. As illustrated in FIG. 1, the chromophores that are fit are oxygenated hemoglobin, deoxygenated hemoglobin, bulk lipid, and water. The chromophores concentrations are also combined in linear combinations to form metrics such as oxygen saturation, total hemoglobin and tissue optical index.

One improvement is integrating a fast measuring continuous wave module to the diffuse optical imaging system. The main advantage over the previous systems is that the continuous wave light would measure the reflectance at many distinct wavelengths at a much higher speed than can be accomplished with the broadband light source and spectrometer. Many of the applications of DOSI involve either measuring an area of tissue to generate an image/map of the chromophore concentrations or measuring a single location for extended periods of time to monitor dynamic changes. With the use of a new faster DOSI imaging system, both dynamic and location based changes could be quantified faster. In order to utilize the potential of a faster sampling system for imaging, the location of the measurement points need to be recorded with the same or higher sampling rate.

Clinical Applications

DOSI has found many applications to measure the concentration of chromophores within a tissue. Due to the tissue homogeneity, and specific depth sensitivity, and low attenuation, breast tissue was targeted as one of the first applications. One of the first applications to breast imaging was to monitor breast cancer tumors during neoadjuvant chemotherapy (O'Sullivan, Leproux et al. 2013). The goal of several clinical trials was to see if measuring changes in Tissue Optical Index (TOI), which is the product of total hemoglobin and water concentration divided by the concentration of bulk lipids, of a tumor could be correlated with pathological response (Cerussi, Hsiang et al. 2007). Another breast cancer study examined the contrast that appeared in tumors within radiographically dense breast tissue (Leproux, Durkin et al. 2013). An interesting application of DOSI has been to measure muscle tissue oxygenation and the how it changes before, during, and after exercise (Ganesan, Cotter et al. 2014). Besides breast and muscle, the brain is also an area of interest that can be measured using DOSI. Brain oxygenation changes during high risk activities such as anesthesia are of interest to researchers because of the difficulty in measuring brain oxygenation noninvasively.

Example 3

Motion Tracking Review

There are many advantages to knowing the motion of objects or people during medical imaging or during normal activity. Many different techniques have been developed that have addressed the accurate capture of human or object motion. Many of the techniques that have been developed were motivated by the entertainment industry in order to create more realistic computer generated images and videos. A few quantitative metrics are used when comparing different motion tracking techniques. A few of these metrics are line of sight requirements, estimated tracking area, quantity of tracked objects, accuracy of tracking, and time resolution.

Electromagnetic Tracking Systems

Figure 2:
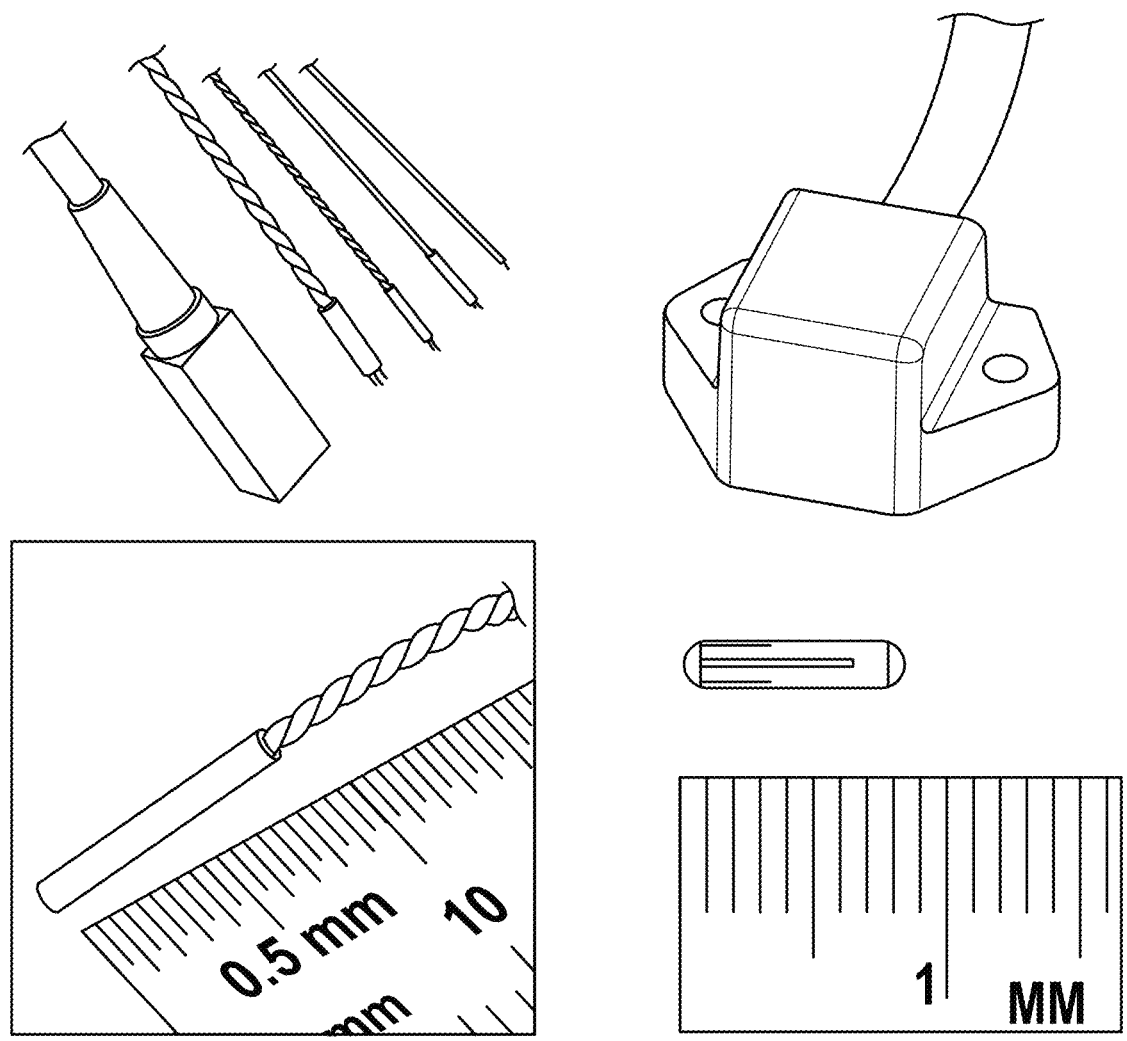
FIG. 2 depicts, in accordance with embodiments herein, examples of magnetic sensors.

One common method that is used in medicine for tracking of objects is referred to as electromagnetic motion tracking. The fundamentals of electromagnetic tracking are straightforward in that a magnetic field is generated by a field generator and small sensors are located within the magnetic field. This type of tracking does not require line of sight of the detectors. The main type of sensors that are used to measure the magnetic flux are search coils, which measure the flux but require an alternating magnetic field, and fluxgate sensors, which can measure both static and low frequency oscillating fields. An example of these sensors can be seen in FIG. 2 herein.

Figure 3:
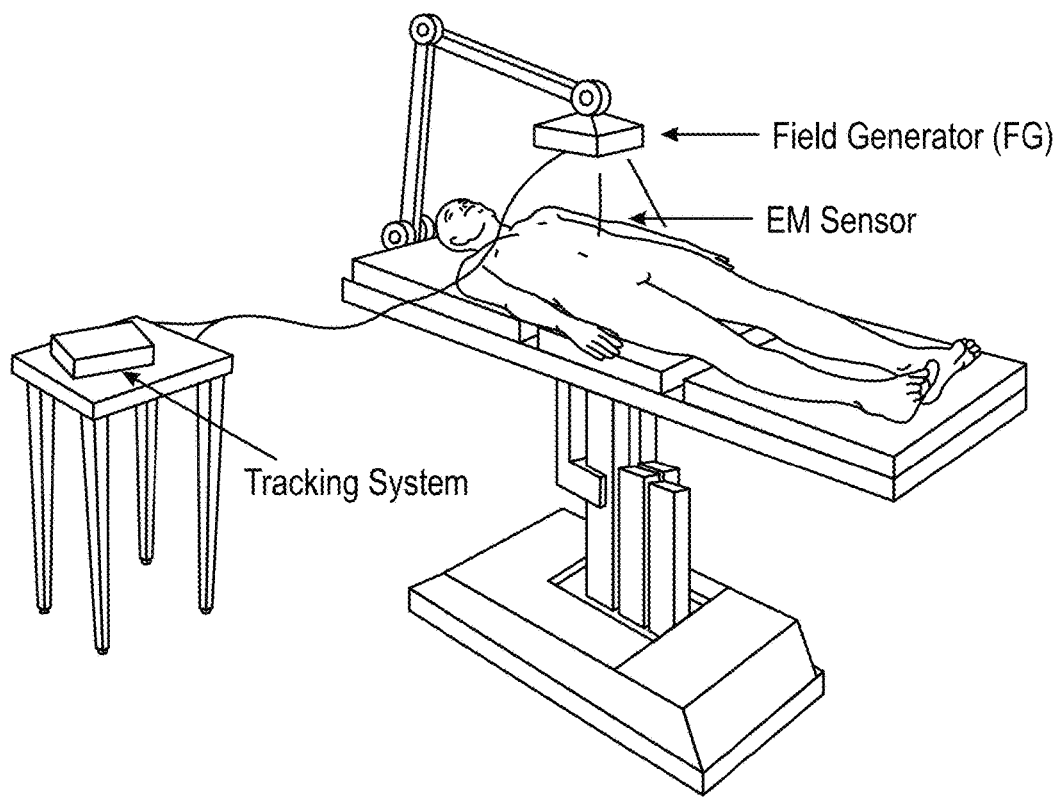
FIG. 3 depicts, in accordance with embodiments herein, an example of intra-operative electro-magnetic (EM) tracking.

The method by which to find the position and orientation of the magnetic trackers can be found in the literature and is different based on the type of sensor and the distance at which it needs to be localized (Schneider 2000). Different techniques may be used for alternating current magnetic field generators than direct current field pulse generators. Many of the sensors can be miniaturized but most still require tethering to a control system. The design of the field generator which generates the various magnetic fields is also highly dependent on the application to which it is used. In most conditions the various systems allow for tracking updates between 40-250 Hz. EM Tracking systems for medical applications have been created and are currently being manufactured by several companies. An overview of intra-operative EM tracking can be seen in FIG. 3 herein.

The two main sources of error for electromagnetic tracking systems are field distortion errors and internal system errors. Internal system errors occur due to limits in accuracy and precision of the generated magnetic field. Many of these errors can be calibrated for using noise reduction methods such as Kalman Filters. Field Distortion Errors are described as any kind of changes in the generated magnetic field that are not internal to the system. The main causes of these field distortions are ferromagnetic material, eddy currents in conductive material, and external currents caused by electronics (Nafis, Jensen et al. 2006).

Achievable tracking resolution can come down to 1.0 mm in environments that are well suited or well thought out for EM tracking. Some of the conclusions based on the review paper of EM tracking discuss why this type of tracking system has not reached critical levels of use in clinics. Reasons why EM tracking has not yet reached critical levels of use in the clinics include lack of robustness of the tracking as well as cost issues with embedding sensors into tools (Franz, Haidegger et al. 2014).

Optical Tracking Systems

Figure 4:
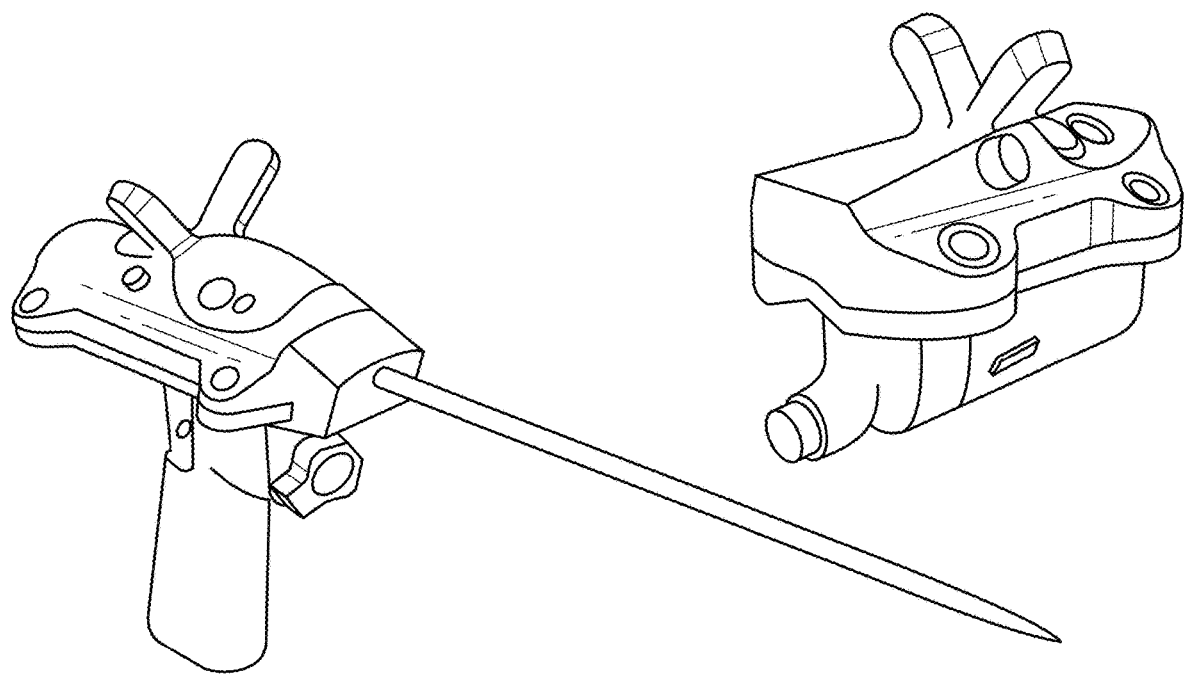
FIG. 4 depicts, in accordance with embodiments herein, surgical tools design for optical tracking.

Another popular method that has been used in medicine is optical motion tracking. There are many different variations of optical motion tracking systems but most of the systems contain the two elements: one or more cameras and object markers. The basic idea is that by using two cameras looking at the same object with known dimensions the motion of that object can be determined with a high degree of accuracy. One of the few drawbacks when using a purely optical tracking system is that a line of sight is required between the object being tracked and the camera. This problem is usually addressed by using specially designed tools or in some cases multiple cameras. Many commercial systems advertise less than 0.5 to 1 mm resolution when using specialized tools. An example of specialized tools can be seen in FIG. 4.

Figure 5:
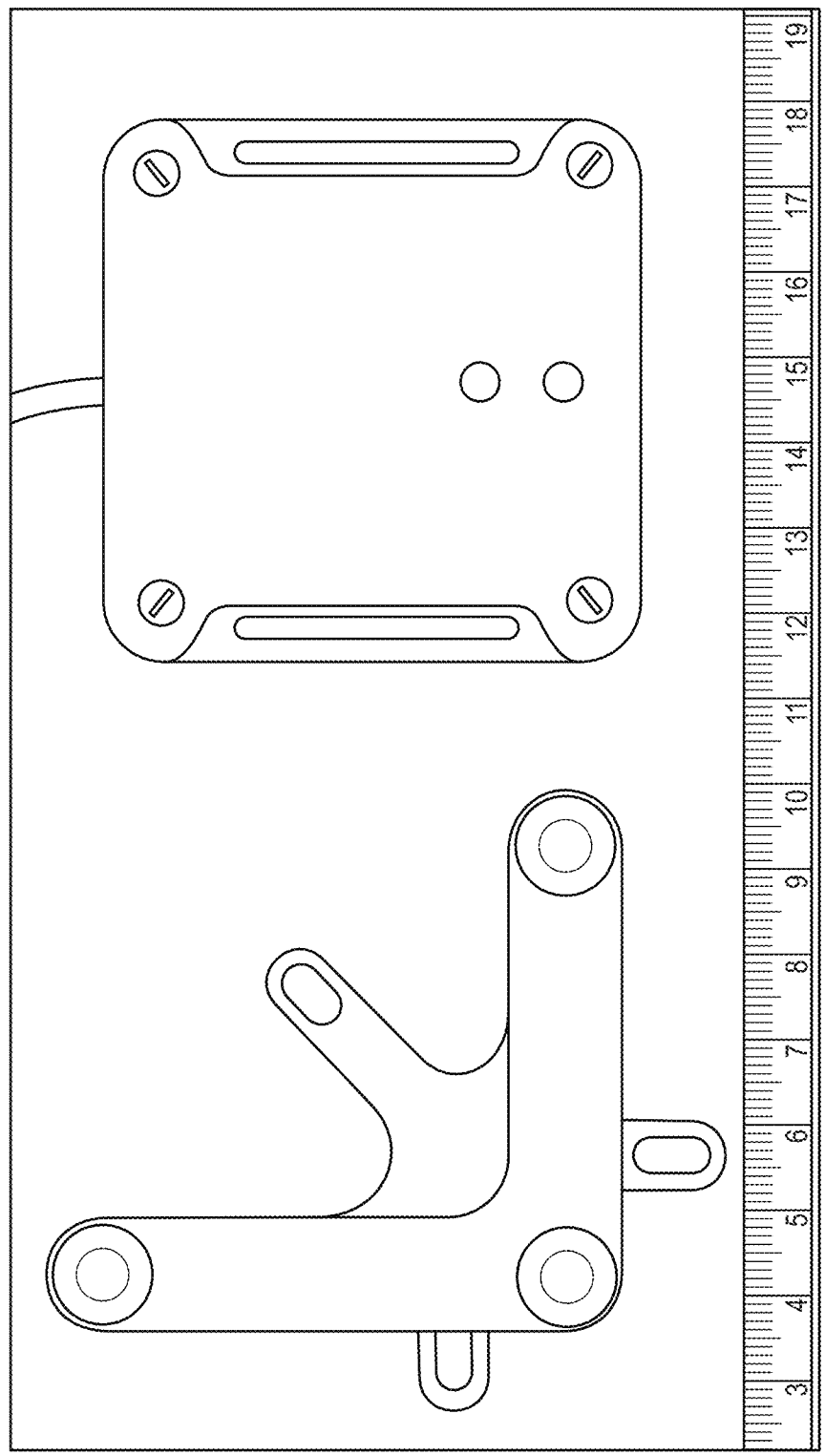
FIG. 5 depicts, in accordance with embodiments herein, optical tracking markers.

A few of the commercially available systems are manufactured by Northern Digital Inc, Brainlab, and Stryker. Many commercial systems have now integrated EM tracking with optical tracking because of the distinct benefits of each system. The assessment of accuracy for optical tracking is the focus of a 2004 research paper by Northern Digital Inc. and the University of Waterloo (Wiles, Thompson et al. 2004). The article suggests that the use of active and hybrid passive systems can have equivalent accuracy if the markers are carefully manufactured. The active and passive markers can be seen in FIG. 5. The error function of these types of system is non-linear over the tracking volume, which can lead to unexpected errors when used by clinicians. Active markers use LED's or some other emitting source to send signals to the camera, while passive markers use reflective markers and make use of the light in the setting.

Optical tracking commercial systems are now used in many applications in surgery because of the high degree of precision that is desired by the clinicians. Applications in orthopedics have been found when aligning implants and screws (Song, Seon et al. 2008). Other applications have also been found in dental surgery (Nafis, Jensen et al. 2006)

Inertial Navigation Systems

Another type of motion tracking that has been developed for many applications is the use of inertial sensors to record and estimate motion. Inertial sensors include accelerometers, gyroscopes, and magnetic compasses that were first developed as mechanical sensors but have now been integrated into MEMS devices. The development of these types of sensors was first motivated for navigation of motion objects such as airplanes, automobiles or ships. These sensors can give information about the local forces and motion of a rigid object. While not traditionally used in tracking of medical instruments, accelerometers and gyroscopes are used to measure activity levels of patients using very simple signal processing. Pedometers are an example of using an accelerometer to measure a simple motion such as walking. Many manufacturers such as Analog Devices (Norwood, Mass. USA), Honeywell (Morristown, N.J. USA), and Invensense (San Jose, Calif., USA) have produced these types of electronic sensors for various applications. The largest application currently is the embedded device market which uses sensors and signal processing to determine when a use is shaking a device or which orientation the device is being held. While inertial sensors may by themselves give relative information, the combination of the sensors with other data allows for tracking of motion within a specific area. The application to measure orientation of an object using only electronic sensors can also be useful for a variety of applications.

Advantages/Disadvantages and Combination Systems

The two main systems that have been reviewed are electromagnetic tracking systems, and optical tracking systems. The use of inertial navigation sensors provides information about the local motion but without the combination of more information is difficult to use for motion tracking. The main advantages of electromagnetic tracking systems are that they are not required to maintain a line of sight during motion tracking, multiple sensors can be tracked with various update information, and precise measurements sometimes under 1 mm in resolution can be determined. The disadvantage of EM tracking is that there are many sources of error, such as the local environment, which can be difficult to easily incorporate into clinical settings. The advantage of optical tracking is that there is a high degree of accuracy when using rigid body objects that have markers. When doing superficial procedures on the surface of the body optical tracking can give less than 0.5 mm of accuracy. The disadvantage is the tools need to be specialized and that they need to maintain a line of sight with the camera.

A few systems have combined motion tracking methods in various ways. The most commercially available systems combine optical and electromagnetic motion tracking and use each method to help correct for errors in the other. Another proposed solution involves the use of EM tracking and inertial sensors for application in surgery (Hongliang, Rank et al. 2012). Most of the systems that have been reviewed are intended for tracking of medical instruments that mainly do not contain specialized hardware, the exception being optical markers. One example of integrating inertial and optical sensors into a medical imaging device can be seen in a novel ultrasound design (Goldsmith, Pedersen et al. 2008). The application that most resembles recording the physical location of an imaging probe is found in the inertial optical instrumented ultrasound system. The drawbacks that need to be improved on are the quality of the orientation measurements, as well as the use of measuring motion on curved surfaces. The system that would most suit the needs of measuring an optical imaging would be to measuring the individual surface of a patient, and use the relative motion of a probe on that surface to register a particular location to the data being generated at that location.

Example 4

Hardware System Design

Figure 6:
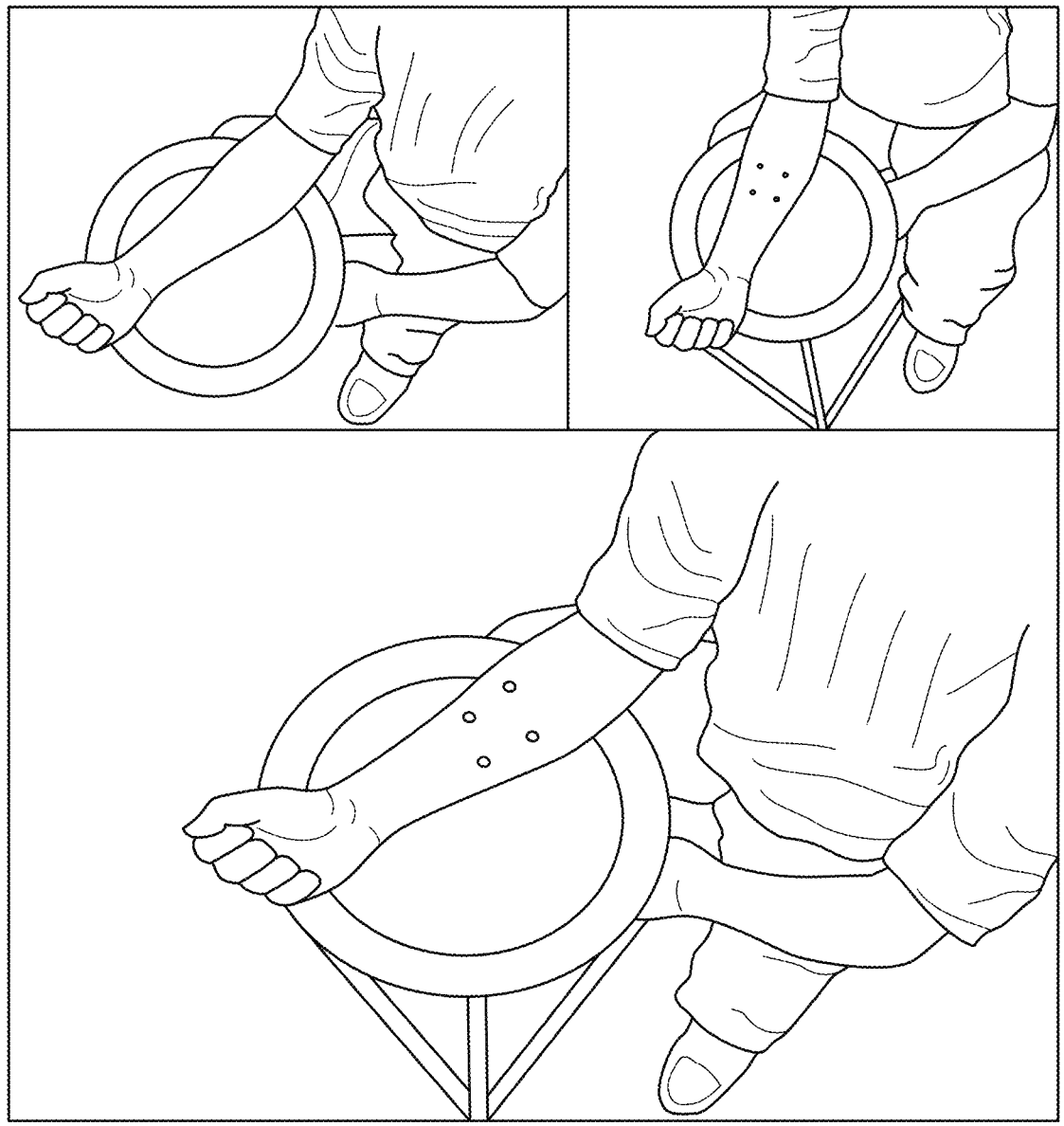
FIG. 6 depicts, in accordance with embodiments herein, an example of kinect fusion process.

In order to record the motion of an imaging probe on the surface of a patient, two types of data were needed. The first type is the surface geometry and texture of the area that was being measured, and the second is the local motion of the probe relative to the surface being measured. This section discusses the hardware design to record these data types.
3D Depth Map Using Kinect A Kinect device (Microsoft Corp, Redmond Wash. USA) was used along with the Kinect for Windows v1 SDK to acquire depth information about a surface. Once the surface was stationary, the depth information output was integrated over time as the Kinect device was slowly moved around the surface. As more depth data points were collected the surface became smooth. While recording the depth information, a color image was saved in order to later add color texture to the surface. After saving the surface information as a wavefront object file, an open source library called Point Cloud Library (PCL) was used to add the color texture to the 3D surface. Fidicual markers used for calibration are placed on the surface and have different color for simple detection on the texture. An example of the Kinect Fusion process is shown in FIG. 6. The example shown is not a perfect map of the texture onto the mesh, but does show the data inputs and steps.
Surface Motion Sensor Selection:
 Linear Displacement In order to quantify the linear displacement of an imaging probe, an optical mouse IC ADNS-9800 (Avago Technologies, San Jose, Calif., United States), was used. The IC and lens system was originally designed for the application of computer mouse for PC video games. The chip contained a VCSEL that illuminated 0.5 mW at 840 nm and a low resolution detection chip designed for high speed data transfer. The detected light was reflected off the surface and imaged on to the detector where it was transferred to an embedded DSP to translate the reflected image into displacement information. The ADNS-9800 could support a frame rate of 12,000 frames per section at a resolution up to 8200 counts per inch. The motion detection was up to 150 inches per second at an acceleration of up to 30 g.
 Rotational Displacement To quantify the rotational displacement of an imaging probe, three inertial motion sensors were used. The 9 Degree of Freedom Sensor stick was purchased from Sparkfun (Denver, Colo., USA) and contained the ADXL345 accelerometer (Analog Devices, Norwood, Mass. USA), HMC5883L compass (Honeywell, city state USA), and ITG-3200 gyroscope (Invensense, San Jose, Calif. USA). The accelerometer chip could measure up to +/−16 g's with 10 bits of resolution, the magnetometer chip had a 12 bit resolution that could sense up to 8 gauss, while the gyroscope could measure up to +/−2000 degrees with 16 bits of resolution.

Figure 7:
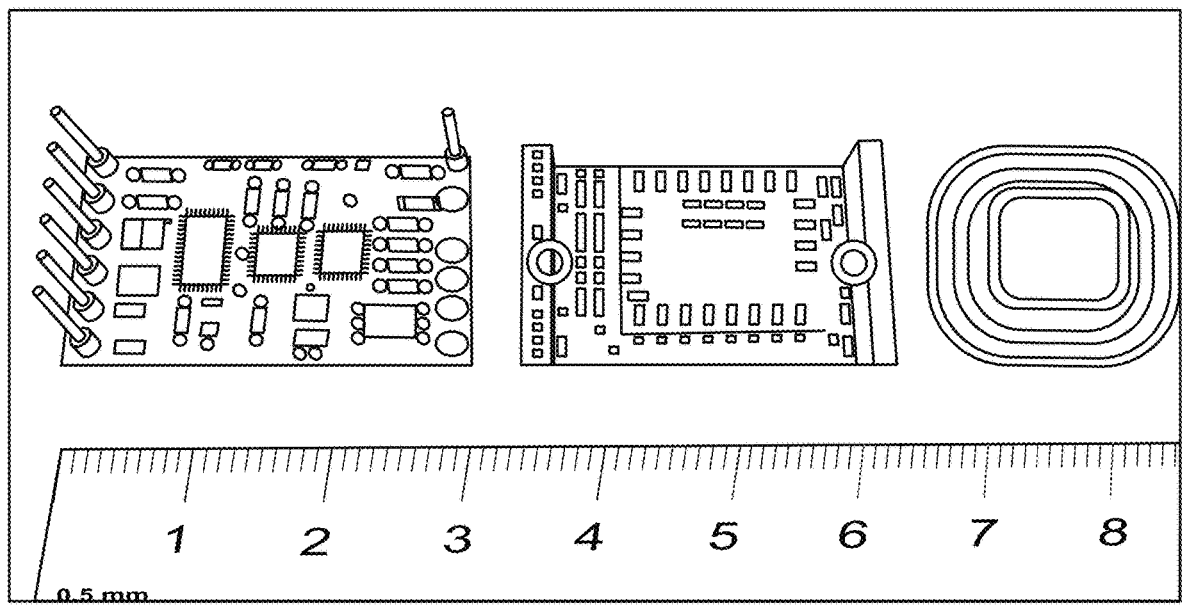
FIG. 7 depicts, in accordance with embodiments herein, redesigned sensor boards.
Figure 8:
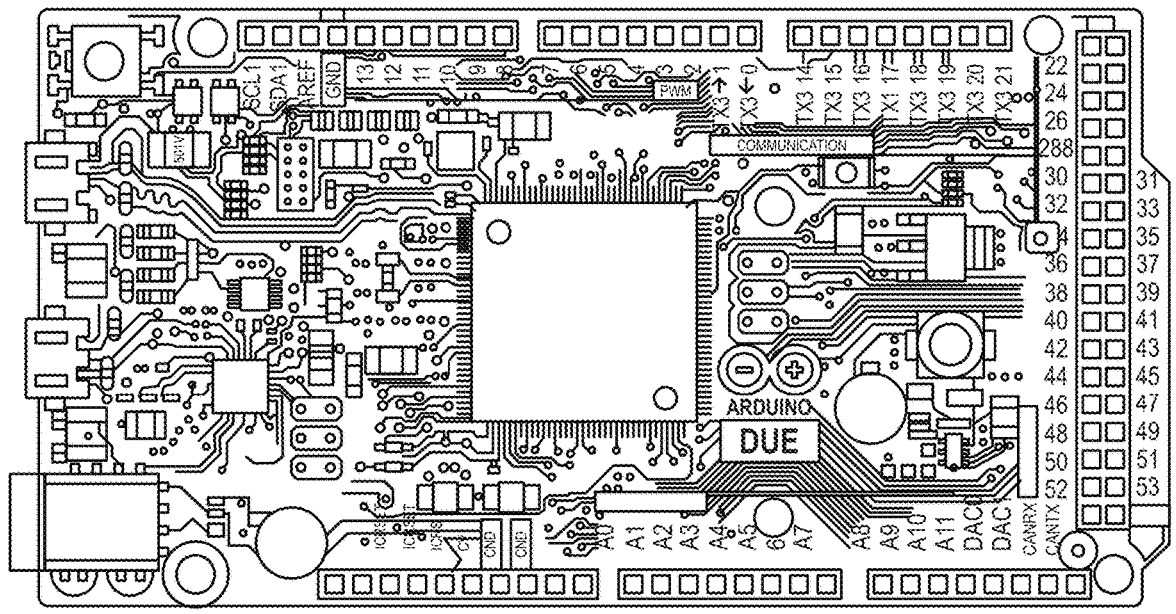
FIG. 8 depicts, in accordance with embodiments herein, arduino due microcontroller.
Figure 9:
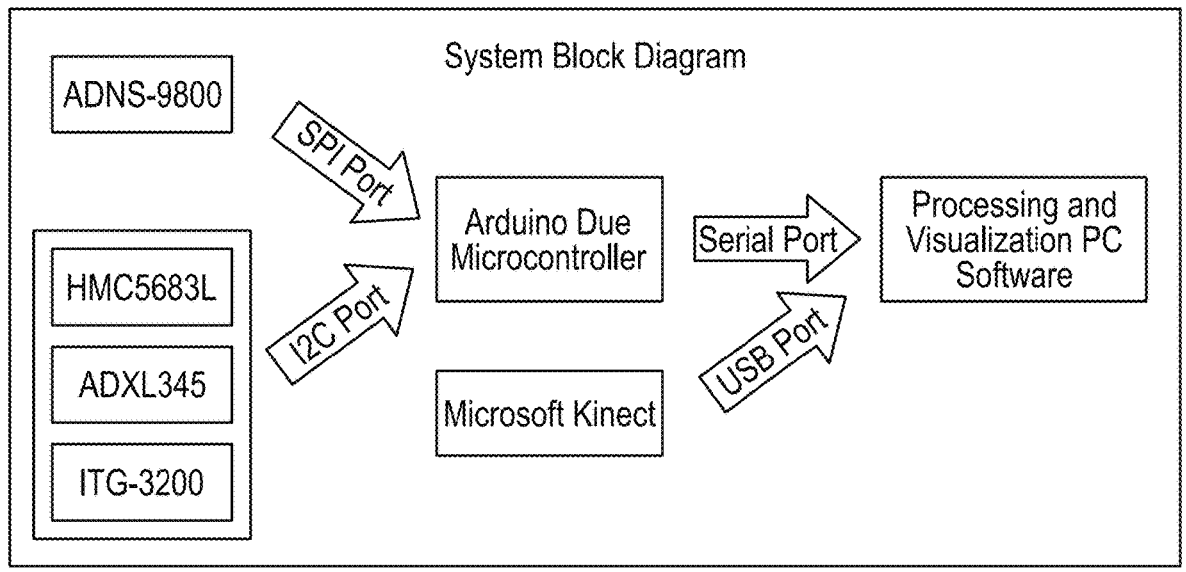
FIG. 9 depicts, in accordance with embodiments herein, an illustrative block diagram for a motion tracking system.

The raw data output of each of these sensors was run through a sensor fusion algorithm based off open source software, Altitude and Heading Reference System. The sensor calibration procedure used was also a modified version from the same source. The algorithm that combines the data is a Directional Cosine Matrix algorithm, which is a simplification of a Kalmann Filter (Premerlani and Bizard 2009). The directional cosine matrix first calculates the magnetic heading. Then the algorithm normalizes the three directional matrices to enforce orthogonality that may be off due to numerical error. The error was estimated and corrected for roll and pitch drift based on the accelerometer, while yaw drift error was based on magnetic heading. Using the DCM algorithm, the orientation of the probe was estimated based on the three inertial motion sensors.
 Combined Sensor Board Originally the two sensors were used on separate boards and the imaging probe was designed to fit both inside. An outside source was used to create a combination board that combined both sensors into a single board set. The motivation behind the redesign was to minimize the footprint of the sensor on the bottom of the probe. In the FIG. 7 herein the redesigned sensor board is illustrated.
Microcontroller and Block Diagram A microcontroller was need for acquisition of the motion sensor data, orientation data sensor fusion, and transmission of the data to the PC. The Arduino Due was selected for this application due to the large open source community of support, built in communication functions and ports, 84 MHz processer and 12 bit ADC/DAC. The Arduino Due is shown in FIG. 7. The ADC and DAC hardware is mainly important for the use with a fast imaging system that needs to be specify the DC power level of the diodes as well as read the output from an amplified photodiode. The Due has the required SPI and I2C ports that are needed to interface the ADNS-9800, ITG3200, ADXL345, and HMC5883L. A block diagram is shown in FIG. 8; the diagram also includes the Microsoft Kinect.
NIR Continuous Wave Imaging System and Probe Design The second key to improving the diffuse optical spectroscopic imaging measurement protocol was to develop technology that could provide faster single location measurements. The slowest part of the single point measurement was the use of a broadband light and spectrometer to get a reflectance spectrum at several hundred wavelengths. This measurement time can be reduced without sacrificing much information as long as there are still reflectance measurements at specific number of individual wavelengths.

The CW diffuse optical imaging system works by modulating NIR laser diodes at moderately high speed. A custom circuit was built that uses internal oscillators at 5-25 kHz to simultaneously modulate the amplitude of the output of the laser diodes. The RF source was filtered to ensure it was only in the correct frequency band then it was added to a DC offset so that the output of the laser diodes had an AC and DC component. A current controlled modulation circuit carried out the modulation. Once the light had passed through the tissue it was detected by an avalanche photodiode and amplified along with band-pass filtered to remove any background light. Using the measuring amplitude of the detected signal the reflectance of the tissue at that wavelength could be assessed. Because the power at each wavelength was much higher than the broadband source and to measuring fewer wavelengths, the reflectance measurements could be taken several orders of magnitude faster than previous systems.

Figure 10:
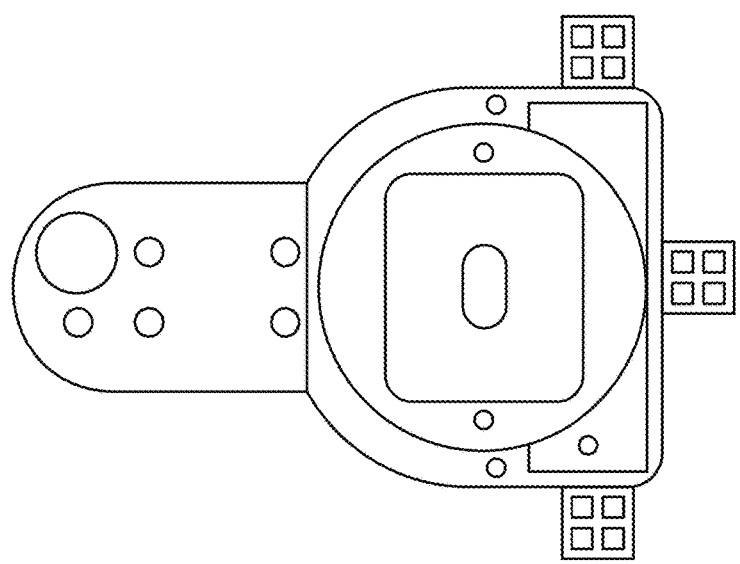
FIG. 10 depicts, in accordance with embodiments herein, an imaging probe model.
Figure 11:
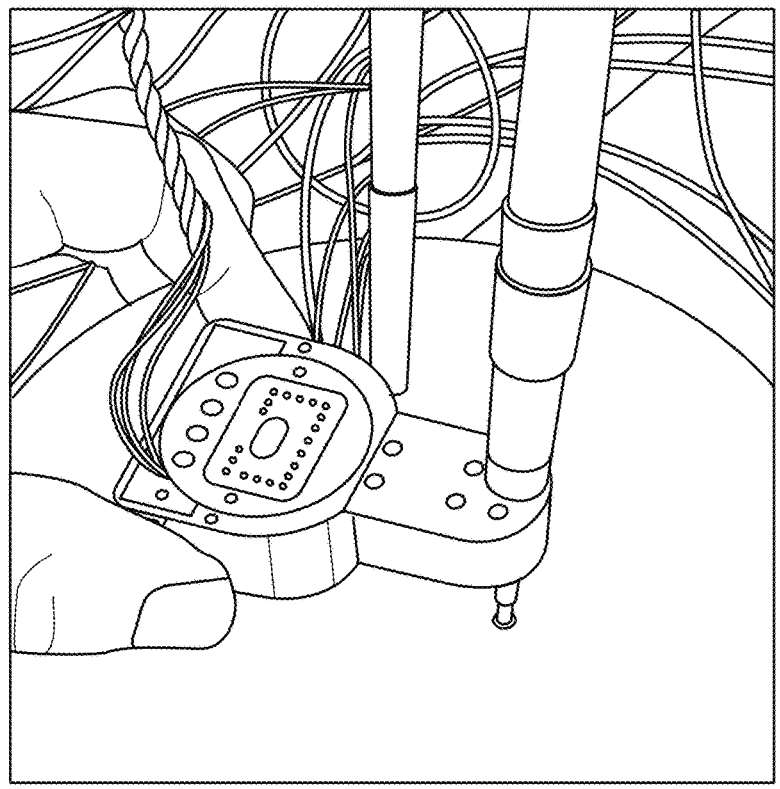
FIG. 11 depicts, in accordance with embodiments herein, fast continuous wave (CW) DOSI probe with tracking hardware together.

The design of the imaging probe needed to be able to support and fix one optical fiber that was coupled to the laser diode light source, and another liquid light guide that was optically coupled to the avalanche photodiode. The distance between the source and detector fiber determine the mean optical path length which the photons go through the tissue. Longer source detector separations let photons go deeper into the tissue but more power was needed to get enough photons to detect. The design of the imaging probe to contain the CW diffuse optical imaging system and the motion tracking hardware is shown in FIG. 10 and FIG. 11 herein.

Example 5

Calibration and Testing

Displacement Calibration

The first step in testing a sensor for displacement was to examine the repeatability of the output. The displacement sensor outputs an integrated count of the displacement in both the X and Y directions since the last time the displacement registers were read by the microcontroller. To quantify the output the data is integrated over the recording window to get a total displacement. To test the consistency of the sensor, the data was recorded and integrated the output while moving along a flat surface by a measured distance. The first sets of tests were done on a plain white piece of paper with distances of 50, 100, and 150 mm. Each trial was repeated five times and the mean and standard deviation of the measured displacement shown in Table 1.

TABLE 1

Table with single path repeatability results, each test was repeated 5 times and the mean and standard deviation of the measured displacement is shown

| | Path Length | | |
|---|---|---|---|
| | 50 mm | 100 mm | 150 mm |
| Mean (STD) | 4067.60 (48.916) | 8358.00 (129.698) | 12265.60 (133.118) |
| Percent Error | 1.203% | 1.552% | 1.08529 |

Figure 12:
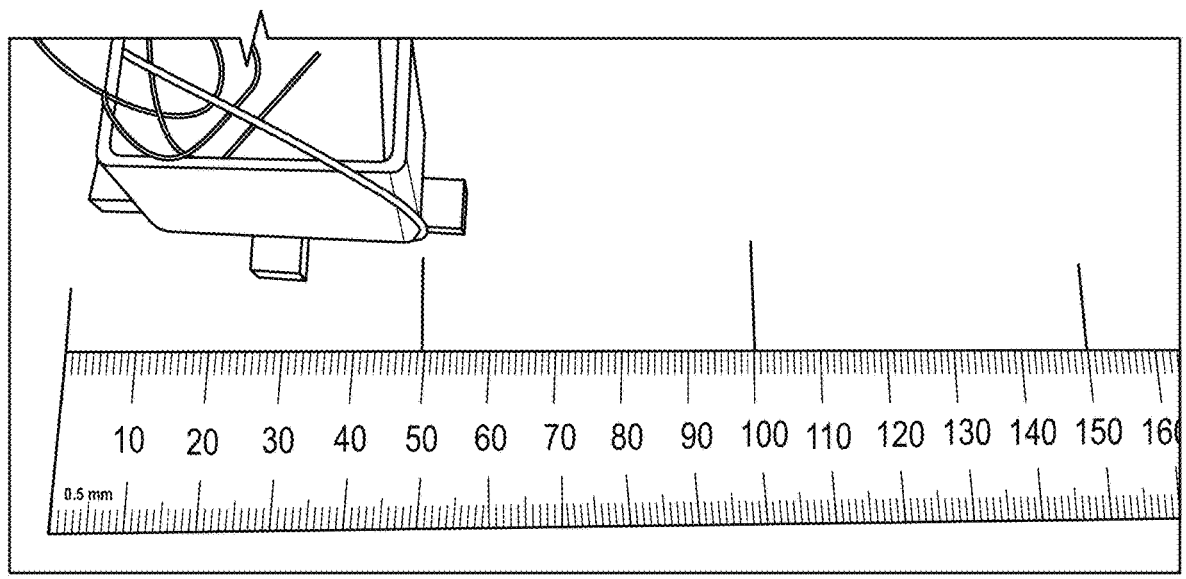
FIG. 12 depicts, in accordance with embodiments herein, an illustrative setup for single path repeatability test.
Figure 13:
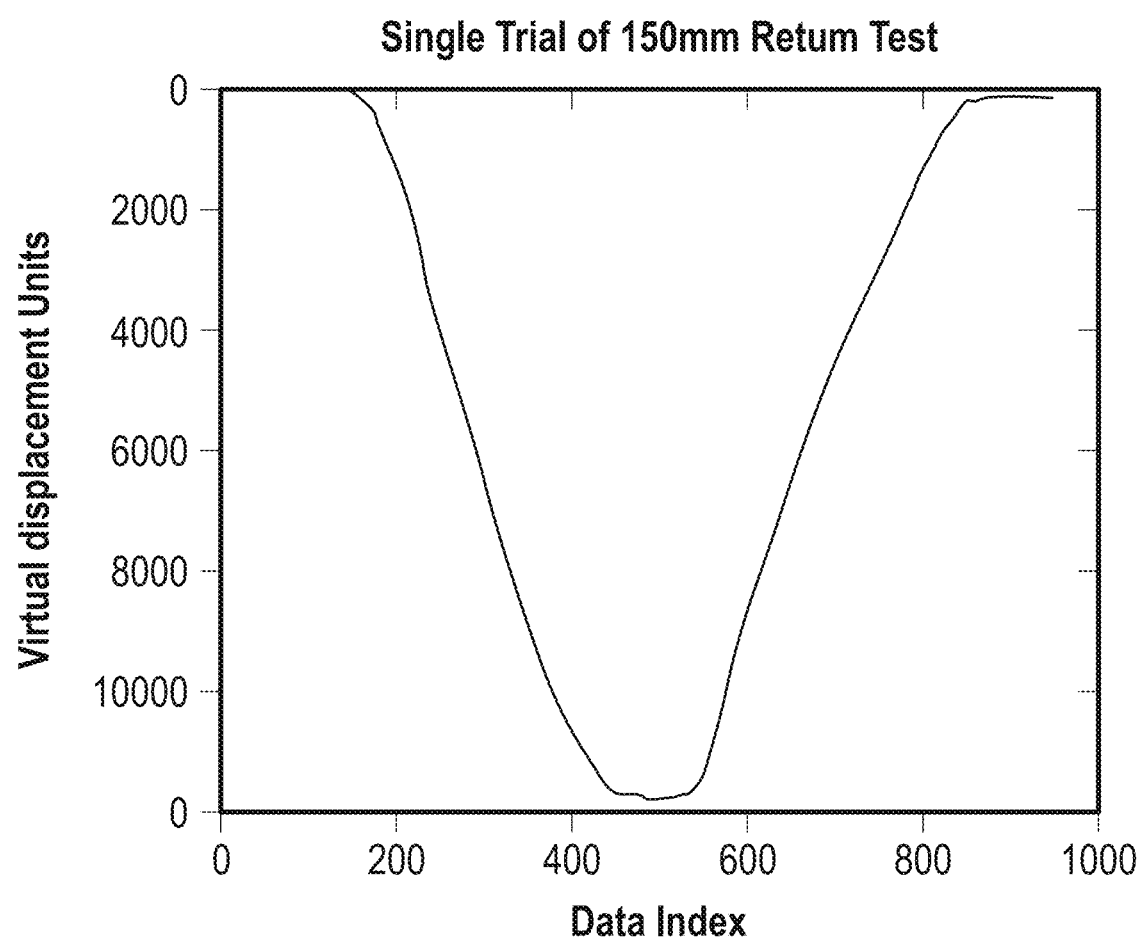
FIG. 13 depicts, in accordance with embodiments herein, an example of integrated displacement data for 150 mm return test.

Another test of interest was to compare the integrated output of two paths of the same length but in opposite direction. This gave an estimate of the accumulated error over multiple paths. Ideally the difference between the two paths would be zero because the net displacement is zero. These tests were performed on the same flat, white piece of paper as FIG. 12 at 50, 100 and 150 mm to the left and to the right. Each test was repeated five times and the mean net displacements along with standard deviations are shown in the Table 2.

TABLE 2

Table with return path repeatability results, each test was repeated 5 times and the mean net displacement and standard deviation of the net measured displacement is shown

| | Return Segment Length | | |
|---|---|---|---|
| | 50 mm | 100 mm | 150 mm |
| Mean Net Displacement | 220.20 (58.709) | 338.40 (148.123) | 291.40 (156.999) |
| Return Percent Error | 1.447% | 1.842% | 1.319% |

Figure 14:
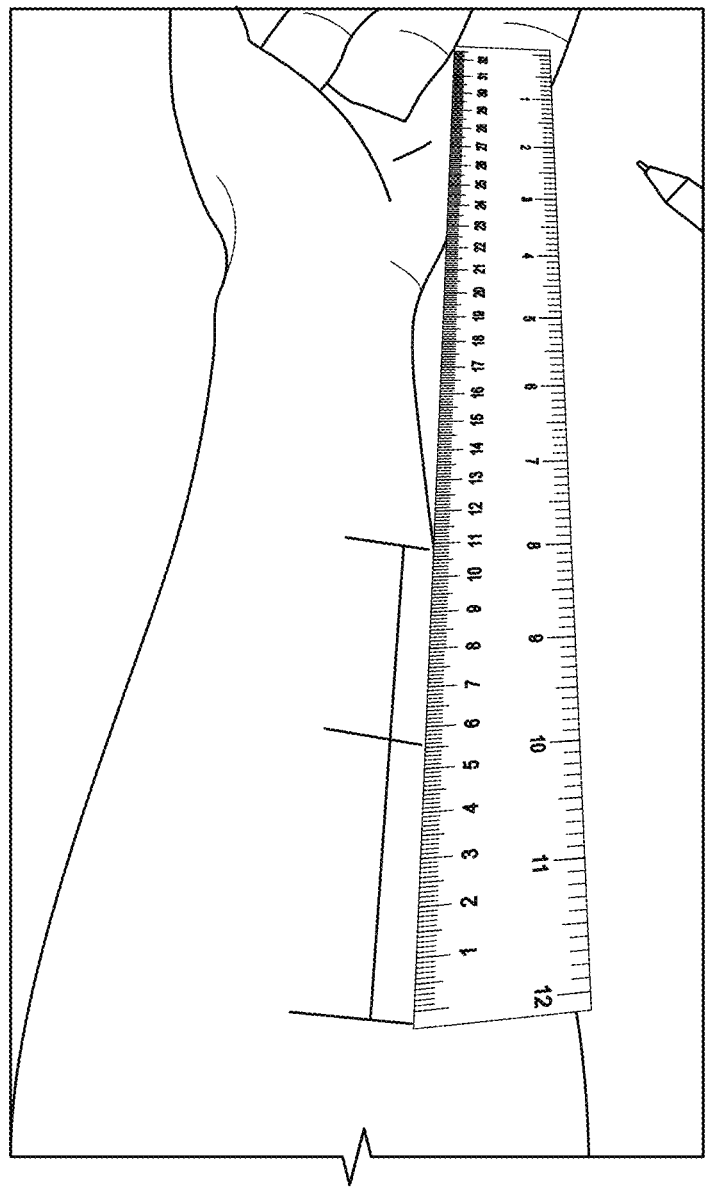
FIG. 14 depicts, in accordance with embodiments herein, an illustrative setup for single path repeatability on skin test.
Figure 15:
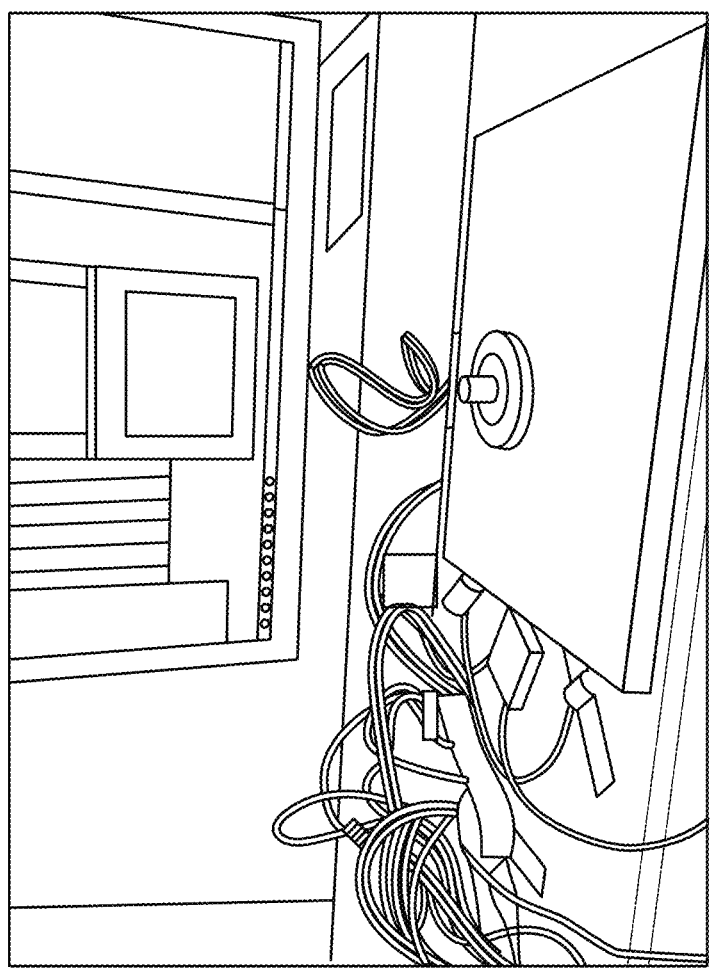
FIG. 15 depicts, in accordance with embodiments herein, an illustrative setup for orientation calibration and tuning tests.
Figure 15:
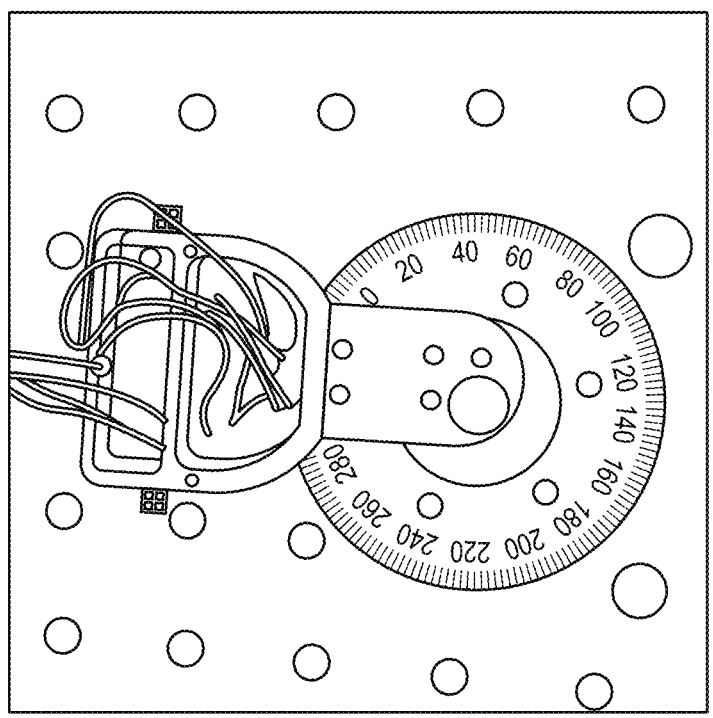
Figure 16:
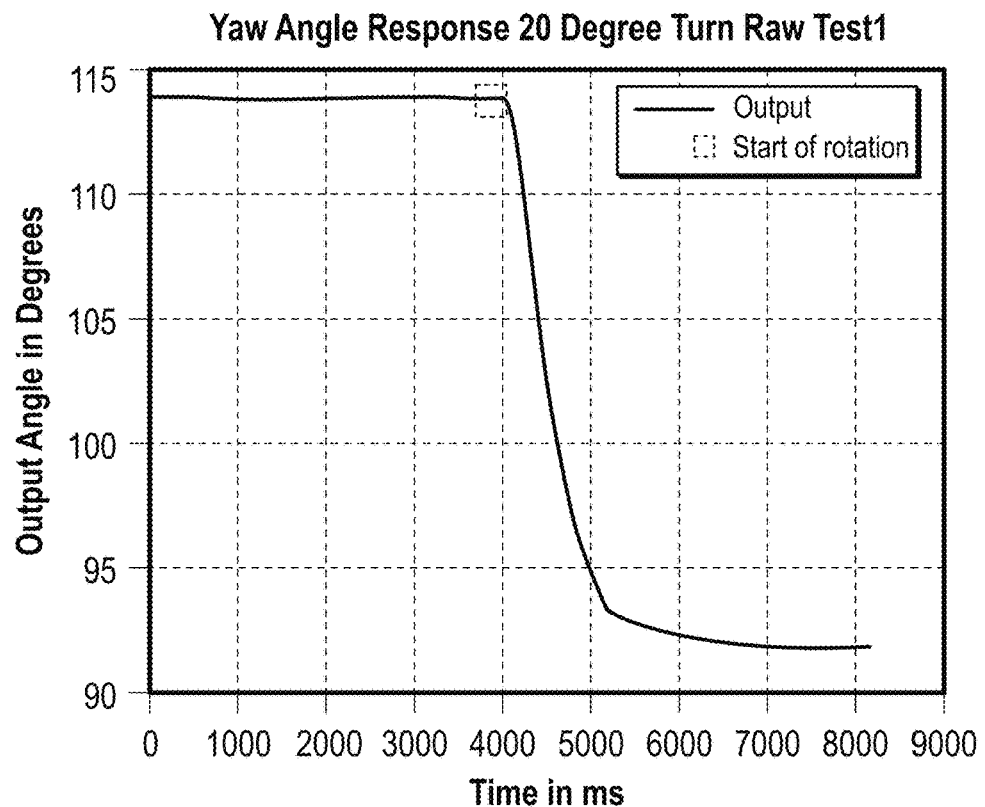
FIG. 16 depicts, in accordance with embodiments herein, an example of results of raw response with standard settings.
Figure 17:
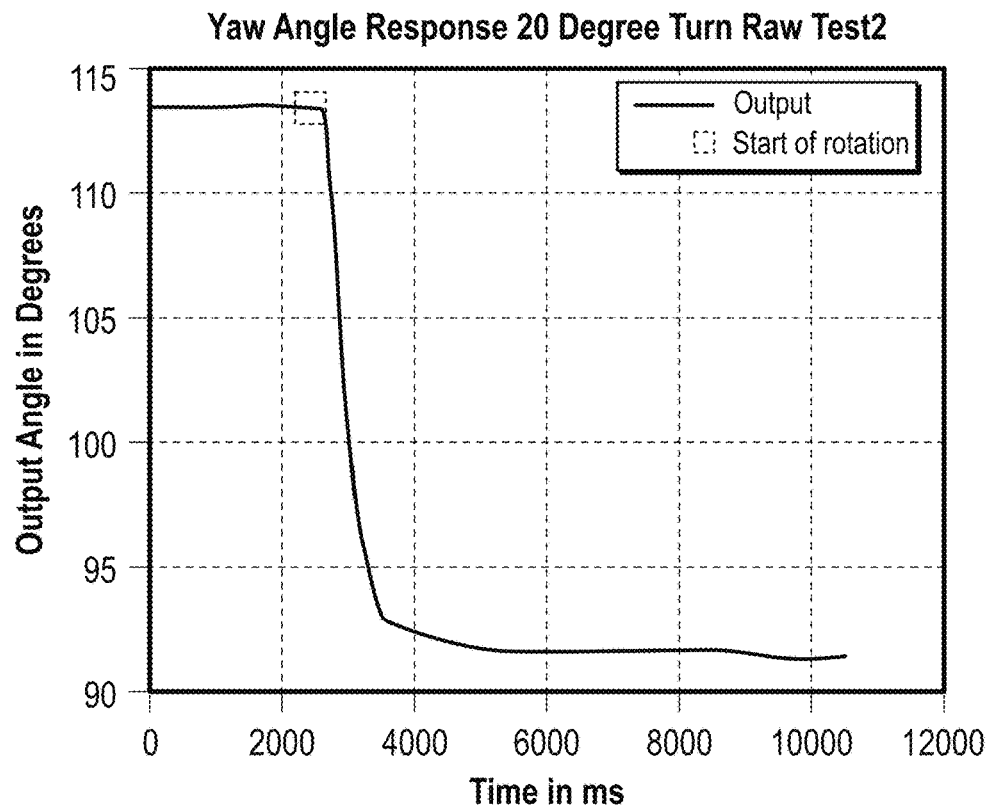
FIG. 17 depicts, in accordance with embodiments herein, an example of results of raw response with longer response time.
Figure 18:
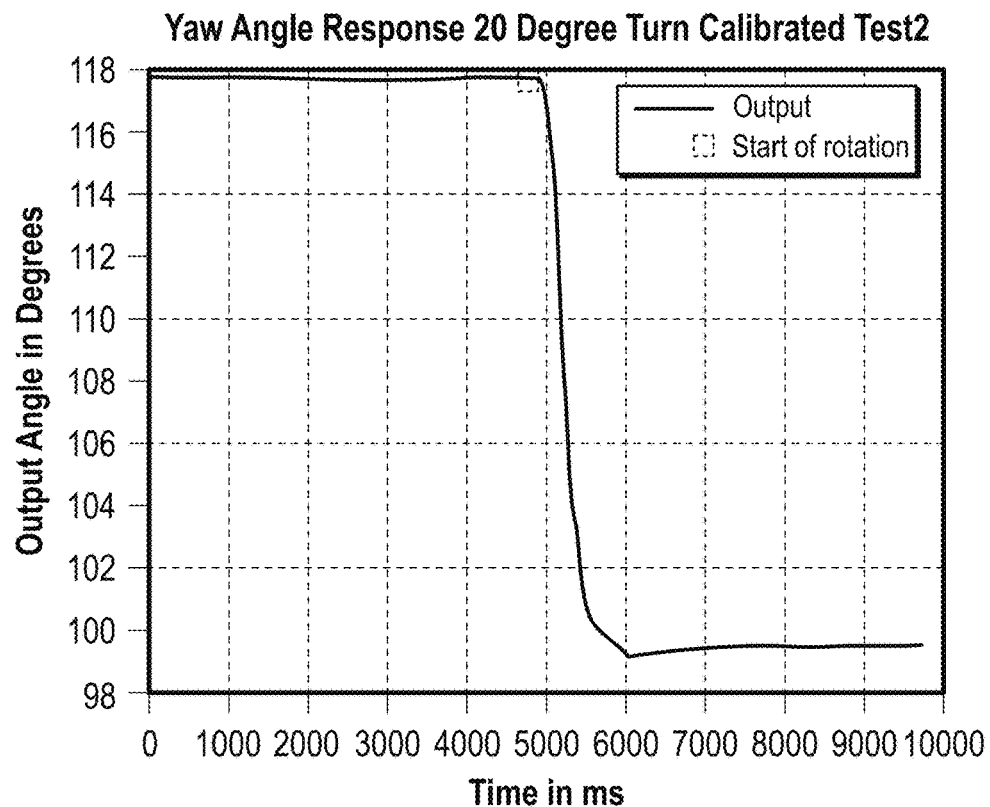
FIG. 18 depicts, in accordance with embodiments herein, an example of orientation response after calibration.
Figure 18:
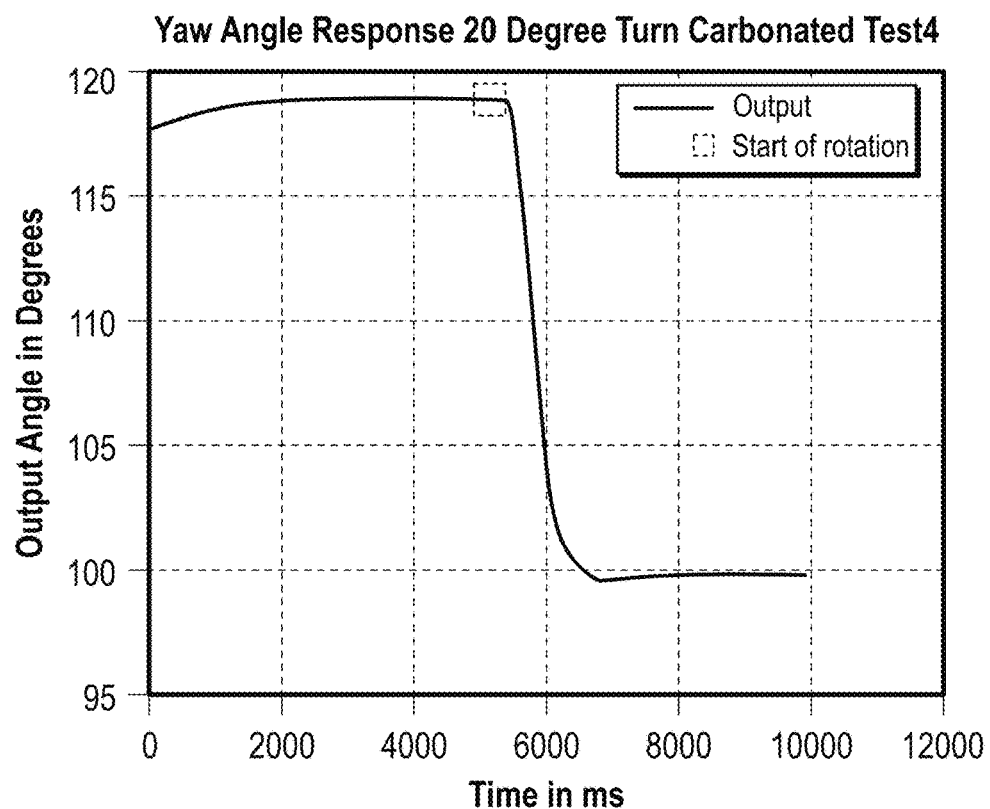
Figure 19:
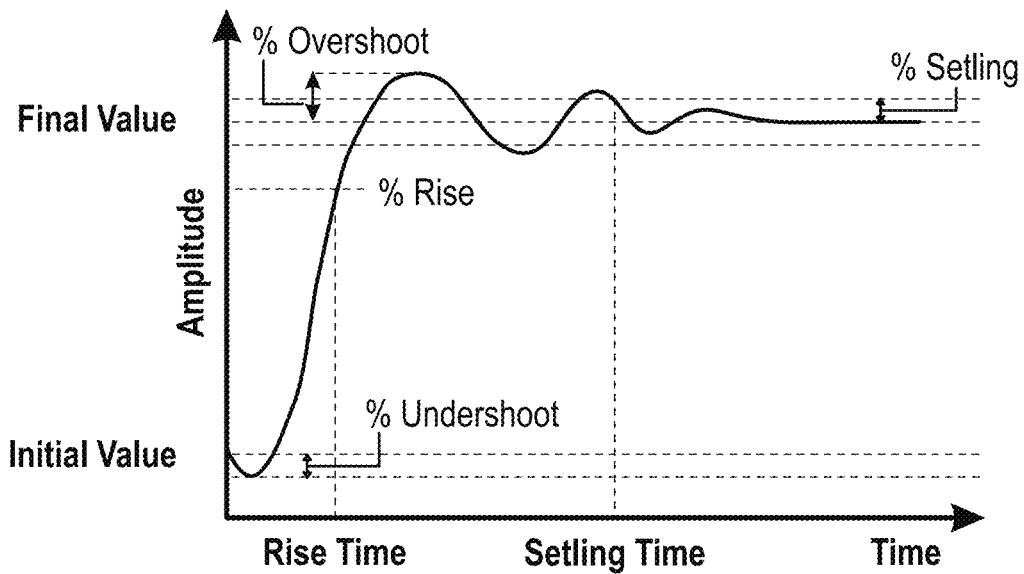
FIG. 19 depicts, in accordance with embodiments herein, an example of control system metrics.

To test whether the displacement sensor could accurately represent distance on the surface of human skin, the initial single path test was done again on the arm of a human subject. Measurements were made with a ruler to mark out 50 and 100 mm lines on the inner arm of the subject. The five paths at each length were recorded and integrated. The setup is illustrated FIG. 14. The resulting measurements similar to Table 1 are shown in Table 3.

TABLE 3

Table of results from displacement repeatability on skin, each test was repeated 5 times and the mean and standard deviation of the measured displacement is shown

| | Path Length | |
|---|---|---|
| | 50 mm | 100 mm |
| Mean (STD) | 3257.00 (118.56) | 6460.80 (201.953) |
| Percent Error | 3.640% | 3.126% |

Based on the results of the displacement tests it appears that the displacement measurement was consistent between trials. The return path tests consistently underestimated the net displacement having positive net displacements in all five trials. The skin displacement tests were on relatively flat skin surface and had consistently higher errors than on the flat surface. Two reasons might contribute to the displacement error on this from this test, the first being the repeatability of the actual test may have been lower because the marker lines were thicker, and the second being the arm may have moved slightly during the measurement. Most likely the repeatability error was due to the repeatability of the test. Thus, in displacement calibrations, more precision motion and markers were used.

Orientation Calibration

Calibrating the orientation sensor was more complicated in that the inventors were mostly interested in the output of a sensor fusion algorithm as opposed to the output from the individual sensors. This led to a two-step calibration process, first to map the raw output of the sensors, second to tune the sensor fusion algorithm to give the best response.

The first step in the calibration process was to characterize the raw sensor value outputs. This process was based off of the calibration method described by described by Peter Bartz of AHRS Razor IMU. The values of interest were the minimum and maximum accelerometer values of gravity in each dimension, the average gyroscope offset in each dimension, and the ellipsoid transform values from the magnetometer.

The second step in the calibration process was to the tune the control values of the DCM Algorithm. The main values that were adjusted were the integral and proportional response constants for the yaw angle. The metrics to measure the response included overshoot, rise time, settling time, and ringing. The second step in the calibration process was independent of the location and local environment, thus only needing to be performed when making system changes.

TABLE 4

Table showing Coefficient value for various tuning tests

| | Tuning Number | | | | |
| --- | --- | --- | --- | --- | --- |
| | Standard | 1 | 2 | 3 | 4 |
| K_proportional | 1.2 | 2.4 | 1.2 | 12.0 | 2.4 |
| K_integral | .00002 | .00002 | .00020 | .00002 | .00020 |

Figure 20:
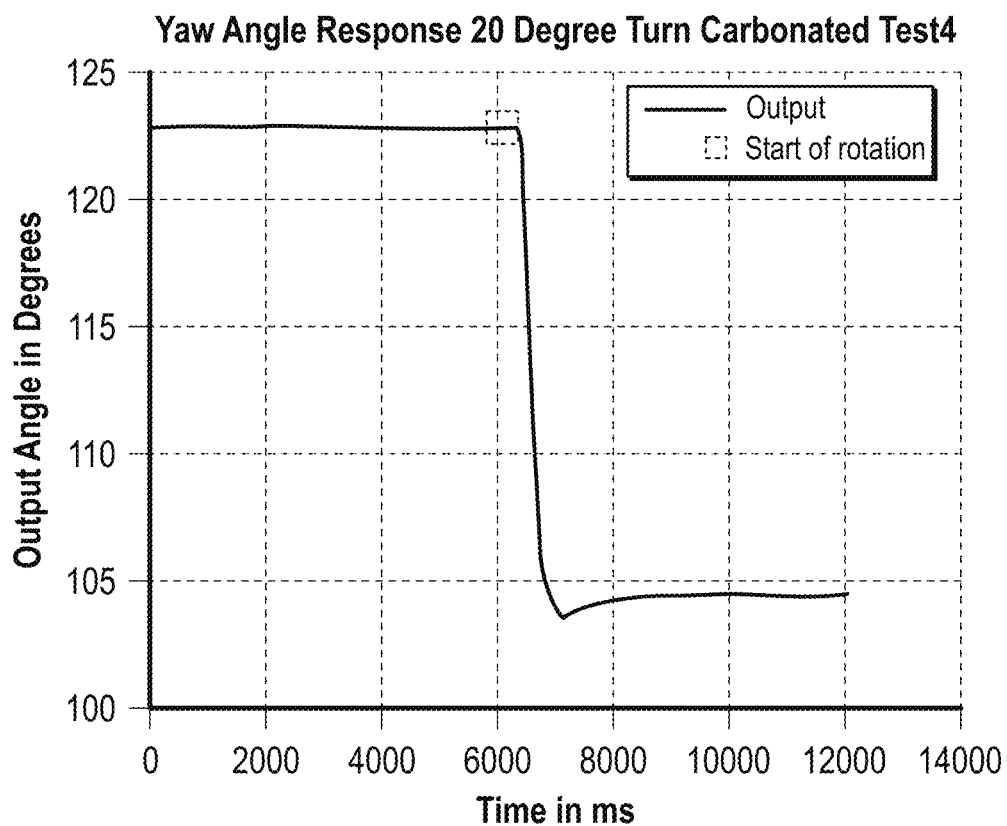
FIG. 20 depicts, in accordance with embodiments herein, an example of response after tuning.
Figure 21:
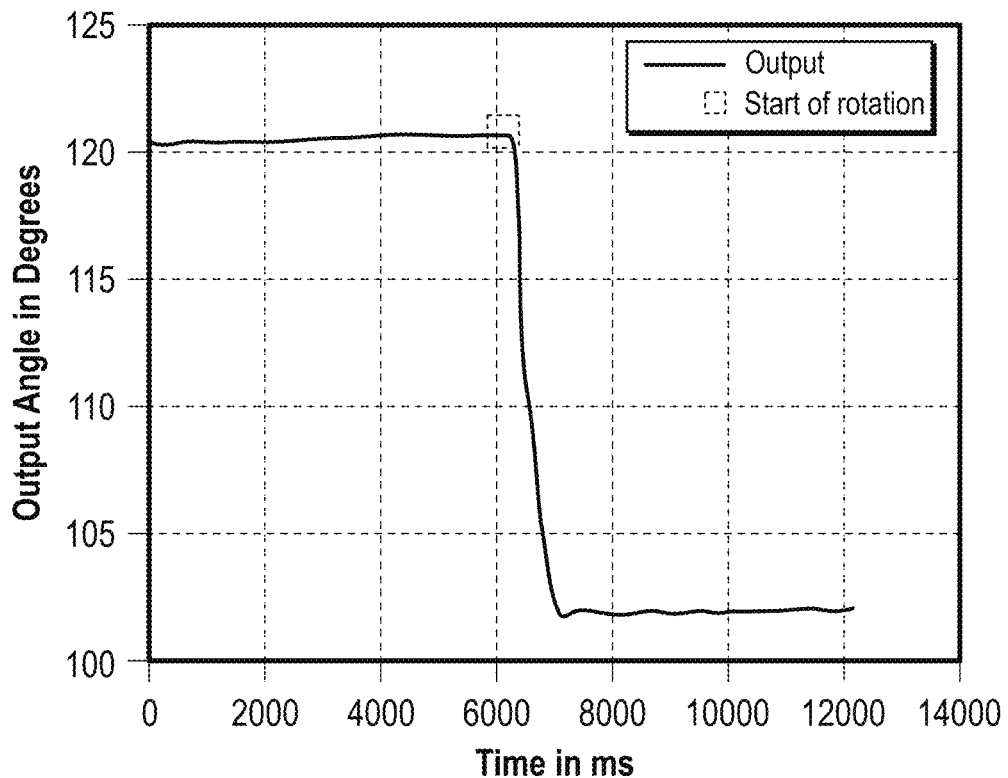
FIG. 21 depicts, in accordance with embodiments herein, an example of response after second tuning.
Figure 22:
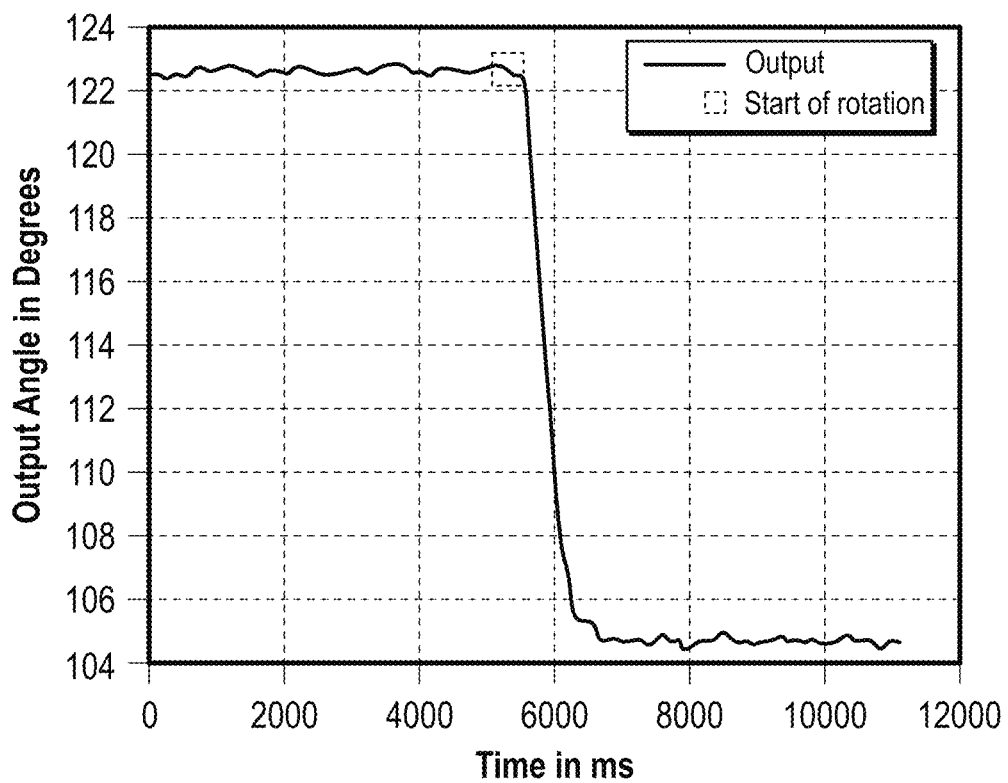
FIG. 22 depicts, in accordance with embodiments herein, an example of response after third tuning.
Figure 23:
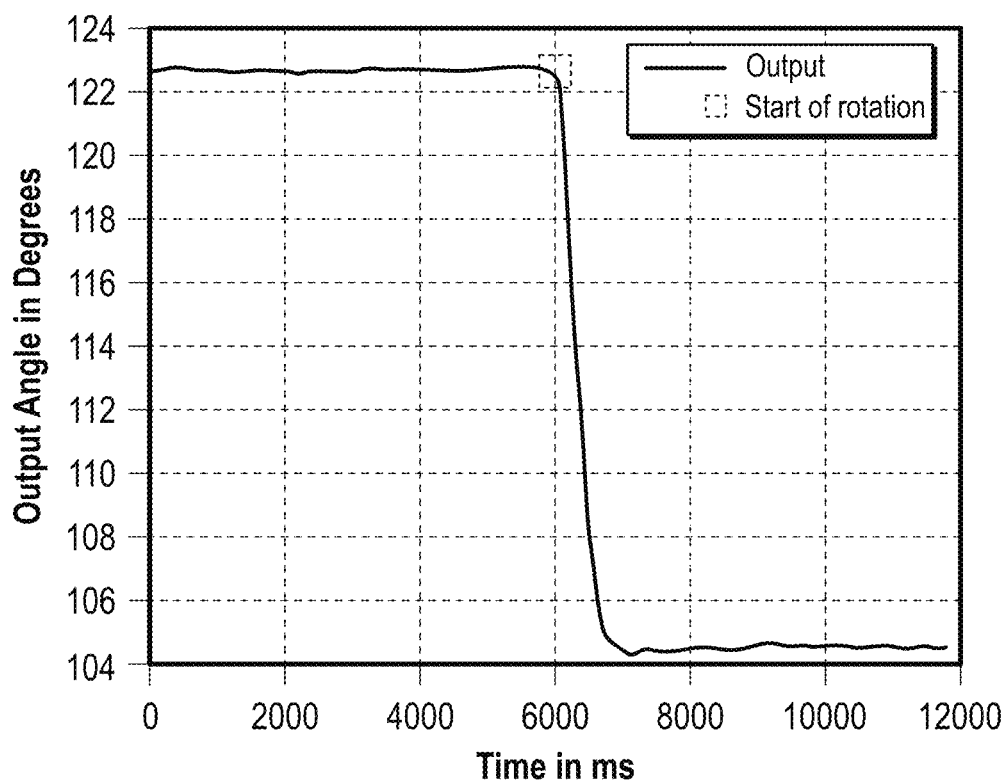
FIG. 23 depicts, in accordance with embodiments herein, an example of response after fourth tuning.
Figure 24:
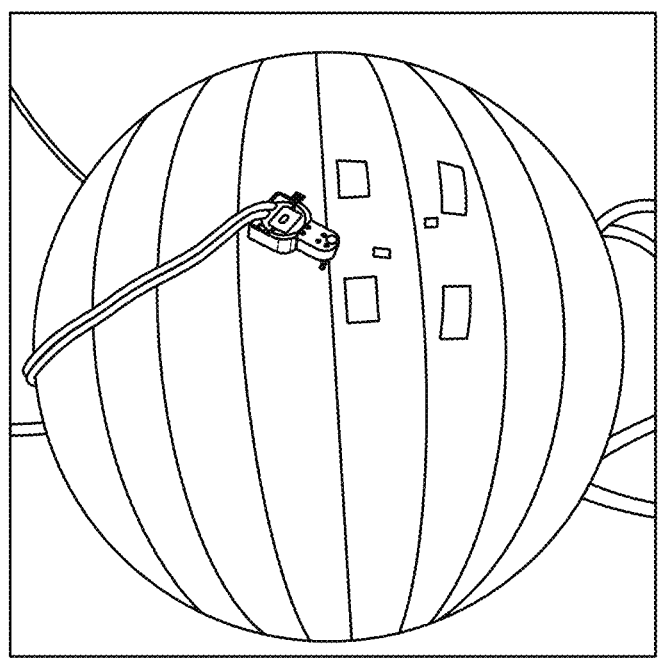
FIG. 24 depicts, in accordance with embodiments herein, an exercise ball tracking surface with calibration points.
Figure 25:
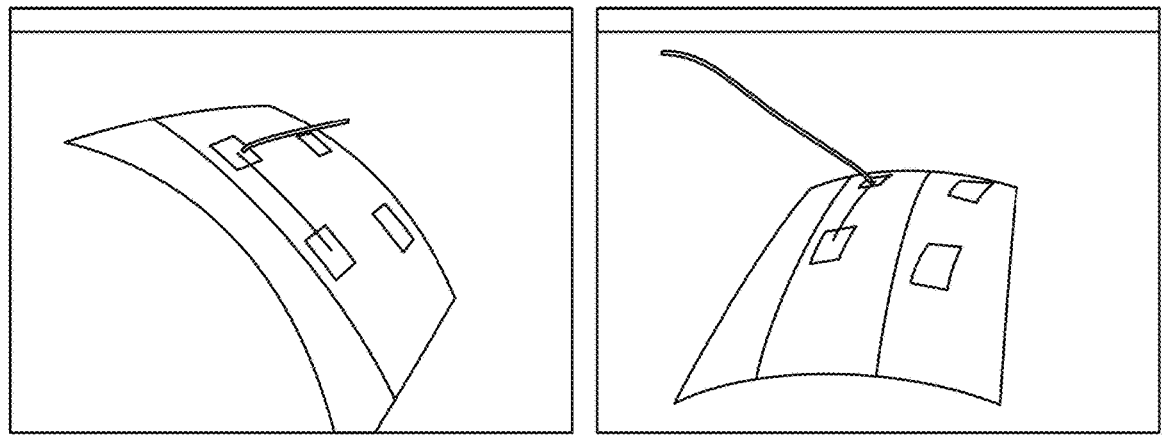
FIG. 25 depicts, in accordance with embodiments herein, rotated and scaled paths using calibration points.

The results of the calibration and tuning significantly improved the response of the sensor fusion algorithm. The calibration of the magnetometer to the local environment showed the most improvement out of the raw sensor calibrations. When tuning the coefficients for the sensor fusion algorithm, the goal was to improve the speed of the response, not have any overshoot, and decrease the settling time. FIG. 20 shows faster response when compared to before tuning by increasing the proportional constant by a factor of two. The second tuning, which increased the integral constant by a factor of ten, reduced the jitter caused in some tests, but led to overshooting the actual value. The third test increased the proportional response by a factor of 10 which caused a lot of jitter in the signal. The fourth and final tuning test increased the integral constant by a factor of ten and the proportional factor by two. The fourth tuning appeared to produce the best response in terms of low overshoot, fast settling time, and fast rise time.

A problem that was found when doing this type of comparison between tunings was the difficulty in reproducing the exact input rotation for the test. A stopwatch or other timer would be useful in helping to control the exact time per degree input rotation. The comparison would also benefit from an analysis script that could give performance metrics, but due to the non-reparability of the test input, that analysis is still qualitative where it should be quantitative and based on metrics.

PC Software Calibration

A custom software program was used to render the motion of the probe on a model in a virtual environment. The main parts of the software included loading in a 3D mesh, calibrating the rotation and displacement to the virtual environment, projecting the measured path of motion onto the surface of the mesh, and visualizing the path of motion as well as the optical data measured by the system.

Example 6

Results and Validation

Flat Surface Tracking

Figure 26:
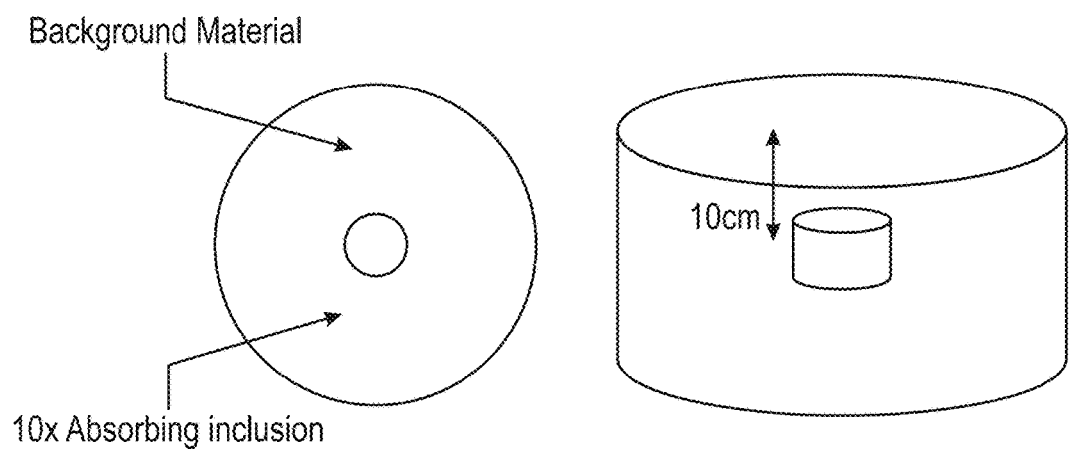
FIG. 26 depicts, in accordance with embodiments herein, an illustrative buried tumor simulating optical phantom. Buried tumor stimulating optical phantom is shown at the top; diagram of phantom with optical properties spatial distribution is shown at the bottom left; image used to texture the 3D scan of the phantom is shown at the bottom right. The probe on the phantom is to show scale.
Figure 26:
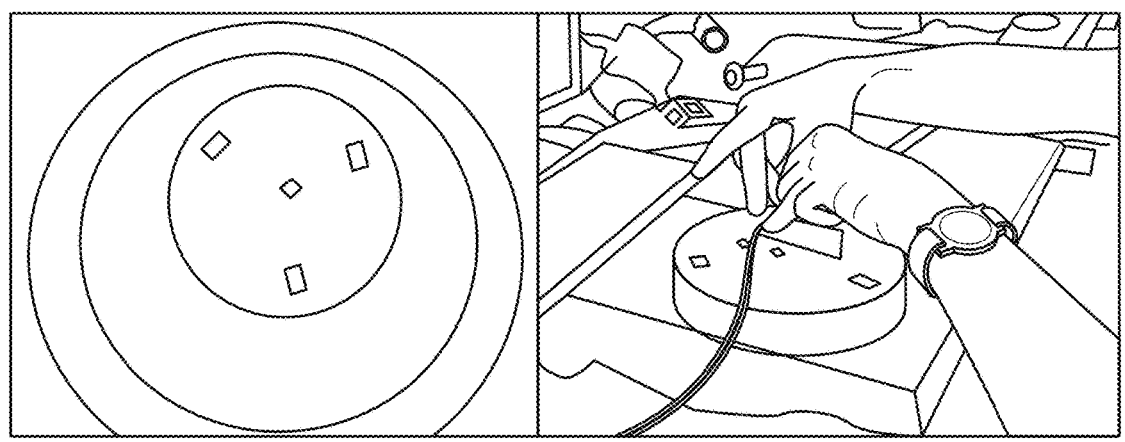

A flat non-deformable surface was the first test of the motion tracking system. Reasons for testing a flat surface included simpler geometry and path projection. Accuracy needed to be estimated and validated before moving to more curved and deformable surfaces. The main flat surface that was used for tracking was an optical phantom with a flat surface. This optical phantom was designed with two materials, a background material with specific absorption and scattering values, and a 10× absorbing material with the same scattering to simulate a tumor. The optical phantom was created so that a small cylinder of 10× absorbing material approximately 10 mm in diameter would be buried 1 cm below the flat surface. The rest of the phantom would have uniform optical properties. A diagram and images of this phantom is illustrated in FIG. 26. Sections of blue tape were placed on the top of the surface as calibration markers to appropriately scale the displacement from real to virtual units. Typical paths were recorded by first placing the probe on top of a calibration marker then moving toward a point of interest or another calibration point.

Figure 27:
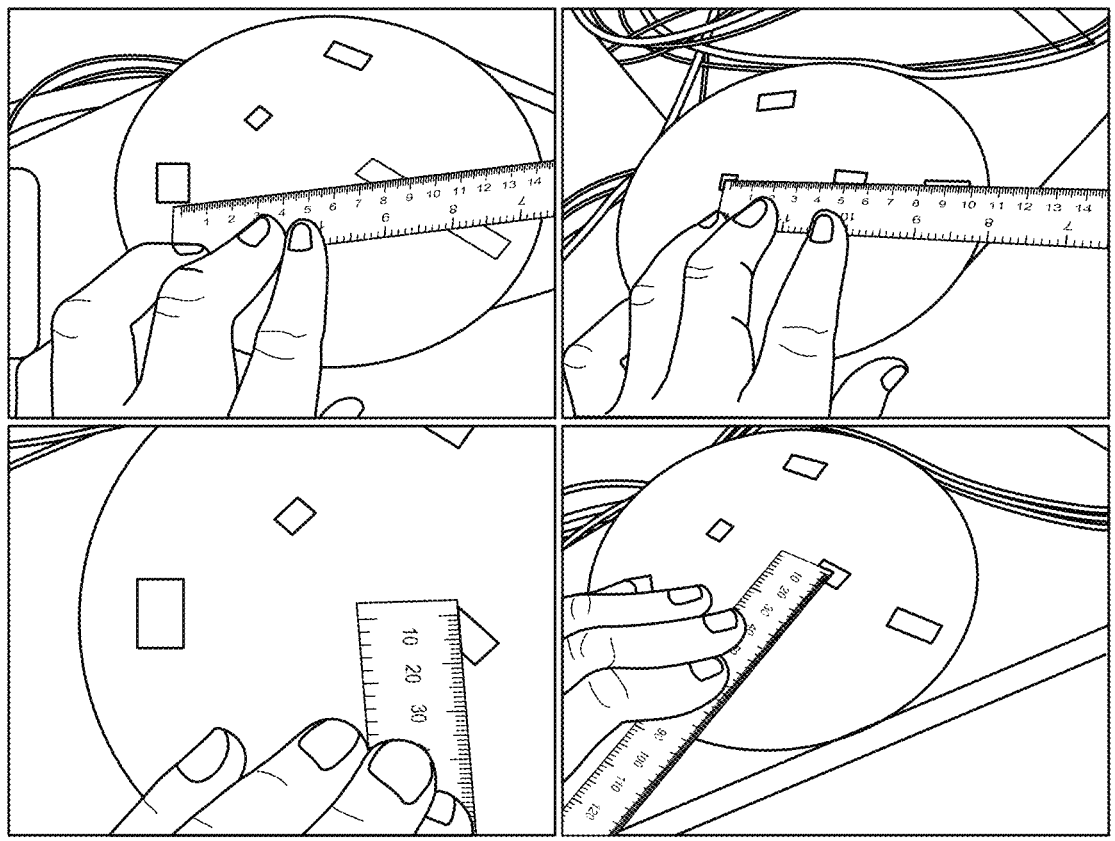
FIG. 27 depicts, in accordance with embodiments herein, buried tumor phantom images of unknown points.
Figure 28:
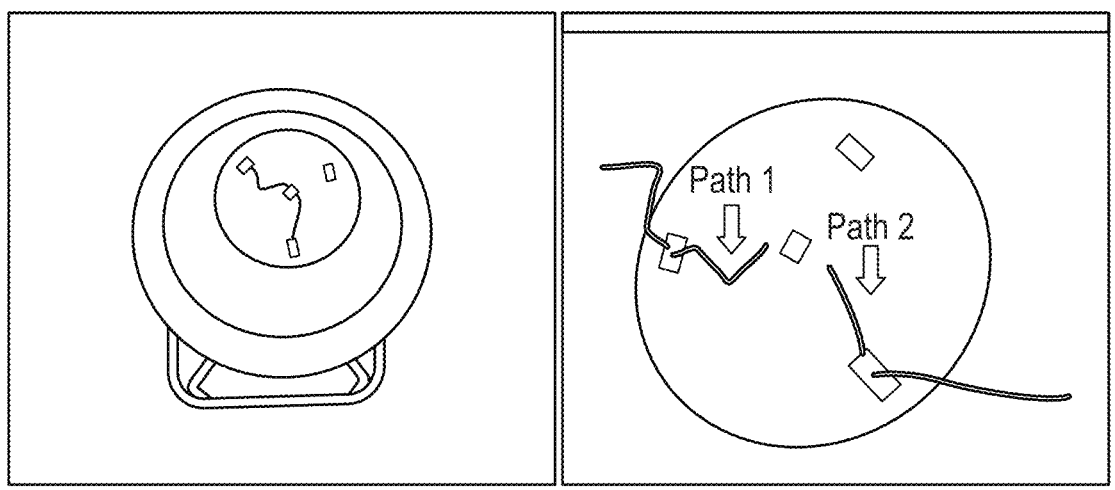
FIG. 28 depicts, in accordance with embodiments herein, unknown point estimation buried tumor phantom.

The motion of the probe was calibrated by moving the probe directly between two calibration points while recording the sensor output. The integrated displacement value was then compared to the measured distance which gave a virtual scale factor. To estimate the accuracy of the system, two pieces of tape were placed on the surface to act as points with unknown virtual locations. A test was performed which recorded the output of the system while moving the probe from one calibration point to the unknown point. This test was important because if the intended use of the system was to record the location of a measurement, the accuracy and repeatability of the location recording needed to be characterized. Images were taken of the surface with a ruler to verify the distances between the calibration points and the unknown points. The images of the buried tumor phantom showing the unknown points along with measurements are shown in FIG. 27. To analyze the results of this test, the virtual distance was measured between the coordinates of the starting calibration point and the coordinates of the final vertex of the path recording. The results of the test are illustrated in FIG. 28 which showed the rendered paths, the black paths were the calibrated (scaled and correctly rotated paths) while the red paths were purely the sensor recordings without rotation. The quantitative results including percent error can be seen in Table 5.

TABLE 5

Unknown point estimation results.

| | Virtual Length | Scale Factor | Predicted Distance | Measured Distance | Error % |
| --- | --- | --- | --- | --- | --- |
| Path 1 | 5.8817 | .08 | 73.5 mm | 47 mm | 56.3% |
| Path 2 | 5.1180 | .08 | 64.0 mm | 48 mm | 33.3% |

Curved Surface Tracking

Figure 29:
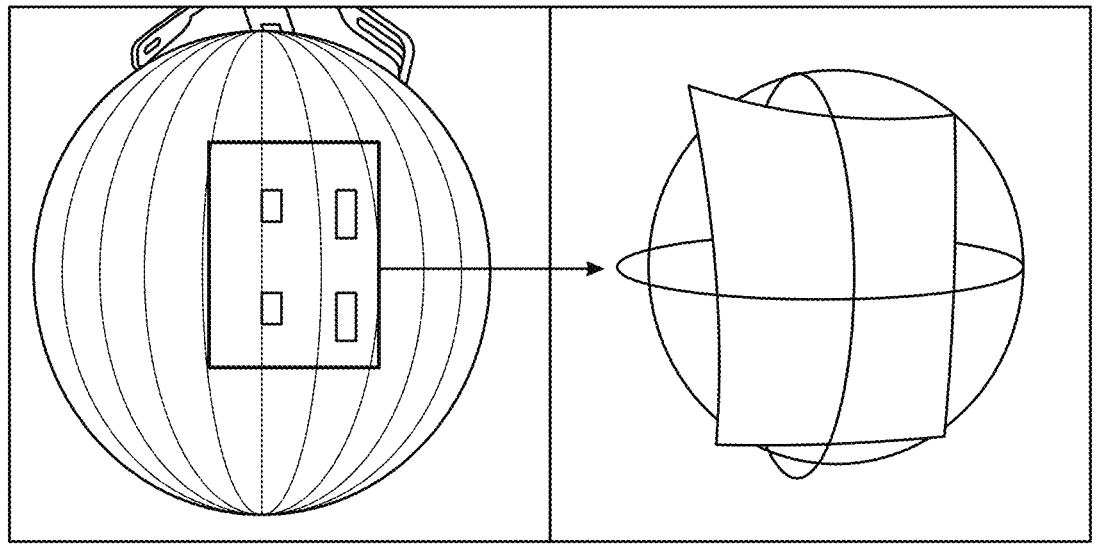
FIG. 29 depicts, in accordance with embodiments herein, an exercise ball model.
Figure 29:
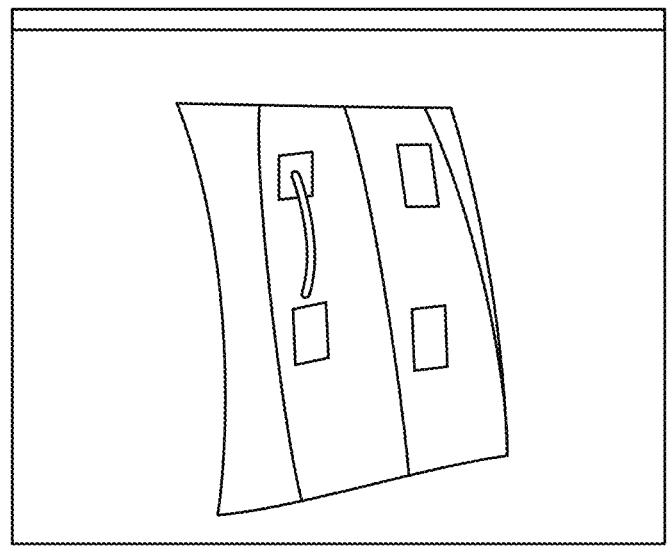

After testing the accuracy of on the flat surface, the next test was to use a curved surface. Two curved surfaces were used to test the motion tracking system, an exercise ball and the human lower leg. The exercise ball is illustrated in FIG. 29 as well as the 3D depth scan and the resulting textured model.

An assessment of accuracy was also done on the exercise ball after calibrating for a virtual scale factor and orienting the path to the surface. Unknown points were marked on the exercise ball and path recordings were generated while the probe was moving from one calibration point to an unknown point. Images were taken of the surface of the exercise ball with the unknown points on them to compare the virtual estimates to the real distance. The measurements of the unknown points can be seen in FIG. 30.

Figure 30:
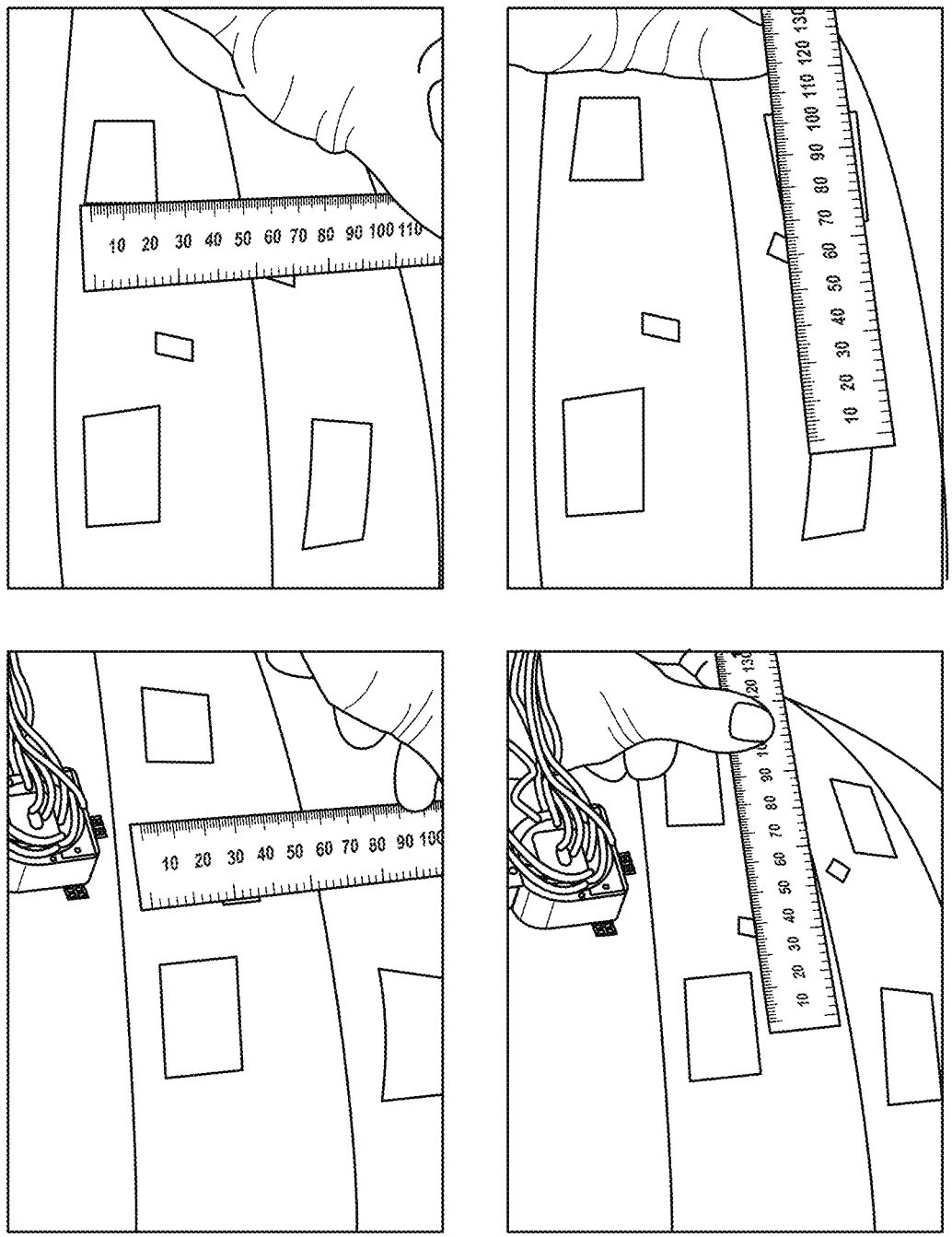
FIG. 30 depicts, in accordance with embodiments herein, an exercise ball with unknown points.
Figure 31:
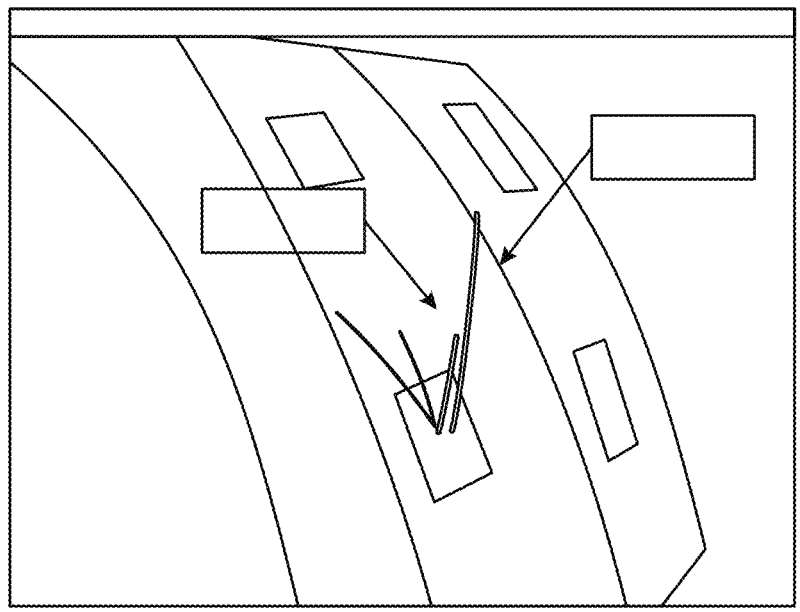
FIG. 31 depicts, in accordance with embodiments herein, path recordings to unknown points.

Renderings of the path recordings to the unknown points can be seen in FIG. 31, while the quantitative results can be seen in Table 6. Both paths shown in FIG. 31 start at the bottom left calibration point as seen in FIG. 30. The numbers generated in Table 6 were generated in the same way as Table 5 using the distance between virtual coordinates of start and end point of the path recordings.

TABLE 6

Unknown point estimation results for exercise ball

|  | Virtual Length | Scale Factor | Predicted Distance | Measured Distance | Error % |
|---|---|---|---|---|---|
| Path 1 | 2.3161 | .0823 | 28.1 mm | 36 mm | 21.9% |
| Path 2 | 4.8619 | .0823 | 59.1 mm | 77 mm | 23.2% |

Figure 32:
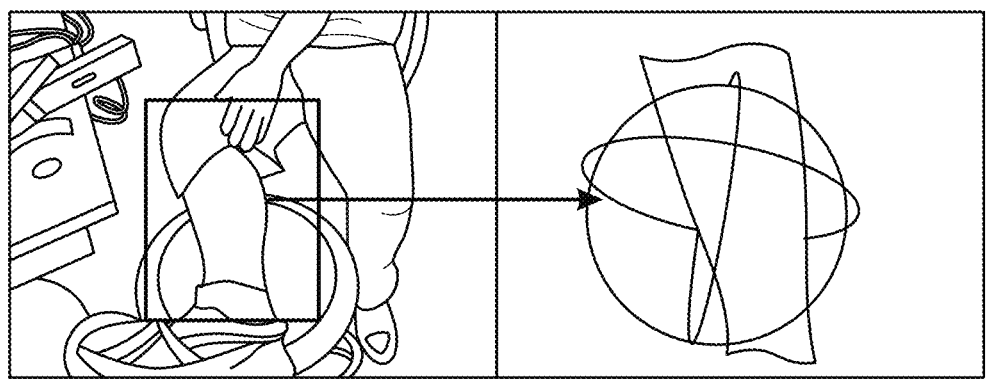
FIG. 32 depicts, in accordance with embodiments herein, a lower leg 3D scan.
Figure 32:
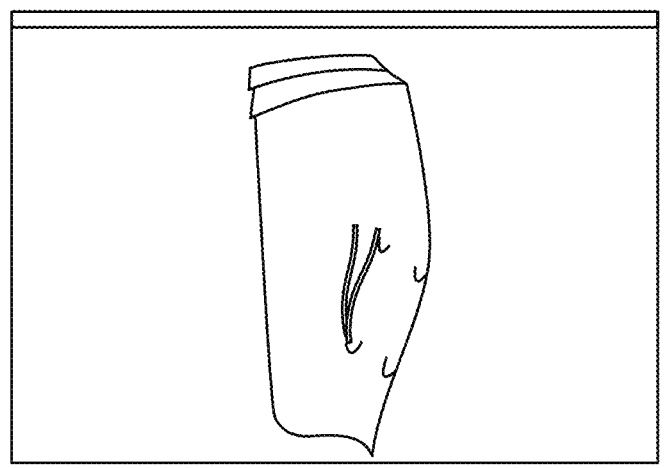

The second curved surface that was used was a human lower leg. The lower leg was marked, 3D scanned, and textured. The results of these steps can be seen in FIG. 32. A rendered calibration path is also shown in FIG. 32 that is a recording of a path where the probe starts at one calibration point and goes directly to another to create a virtual scale factor.

Figure 33:
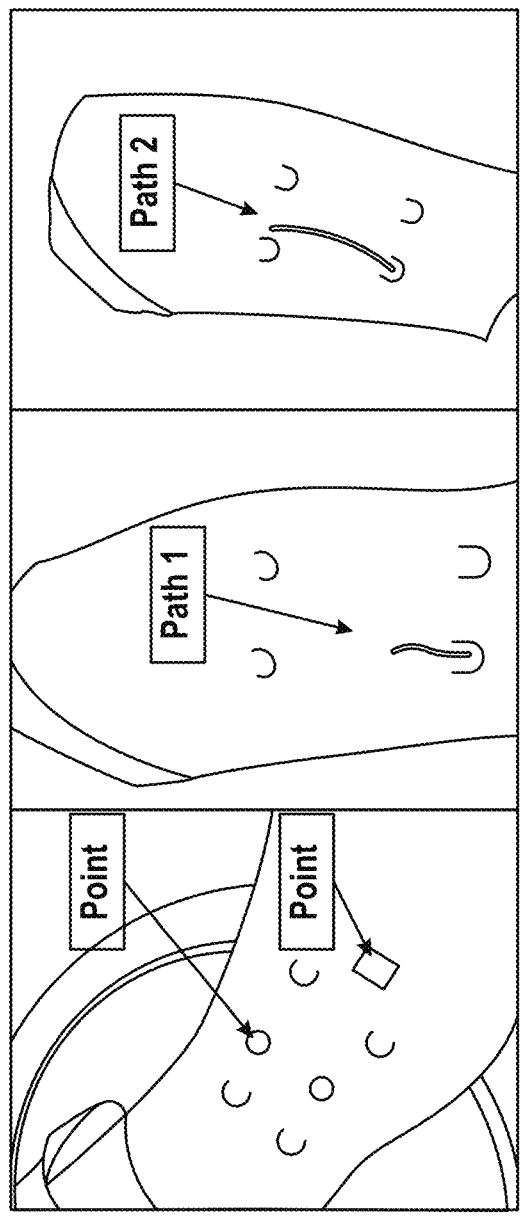
FIG. 33 depicts, in accordance with embodiments herein, lower leg unknown points and path recordings.

The unknown points that were marked on the lower leg can be seen in FIG. 33. Path recordings were taken while moving from the bottom left calibration point unknown point 1 and unknown point 2. Renderings of the path recordings can be seen FIG. 33. The path recordings were analyzed in a similar manner as the other accuracy tests by taking the distance along with surface between the calibration point and the predicted path endpoint. The results of that analysis is shown in Table 7.

TABLE 7

Unknown point estimation results for lower leg results

|  | Virtual Length | Scale Factor | Predicted Distance | Measured Distance | Error % |
|---|---|---|---|---|---|
| Path 1 | 1.1312 | .12 | 11.0 mm | 27 mm | 59.2% |
| Path 2 | 4.7882 | .12 | 39.9 mm | 70 mm | 43% |

Optical Measurements

Figure 34:
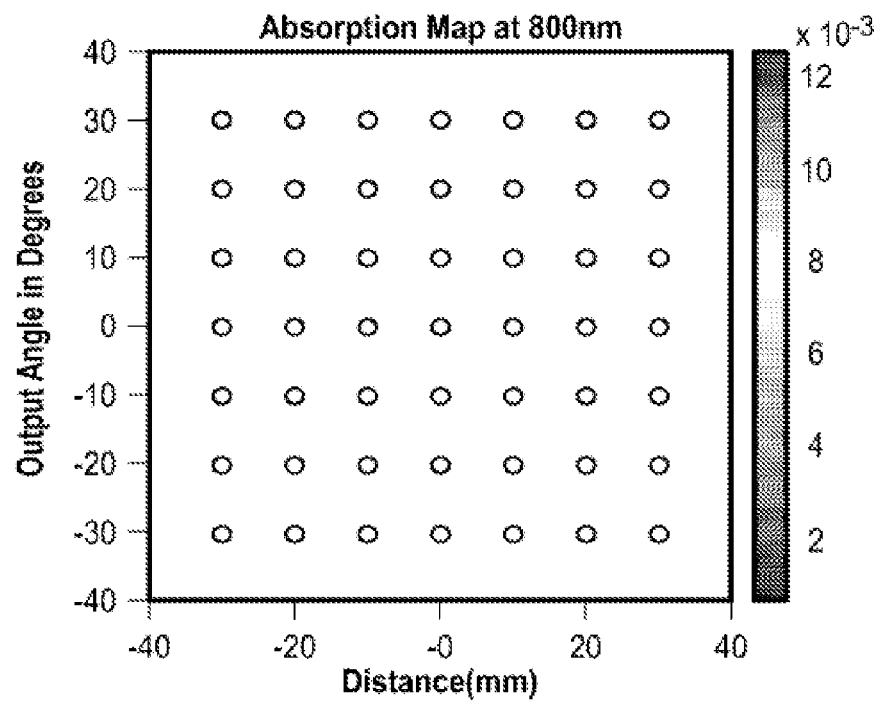
FIG. 34 depicts, in accordance with embodiments herein, optical measurement comparison of tumor phantom. Absorption at 800 nm measurements using the FDPM/Broadband DOSI system is illustrated at the top left; absorption measurements with high speed CW system is illustrated at the top left; and a diagram of the buried simulating phantom is illustrated at the bottom left; and higher density scan of square in ROI is illustrated at the bottom right.
Figure 34:
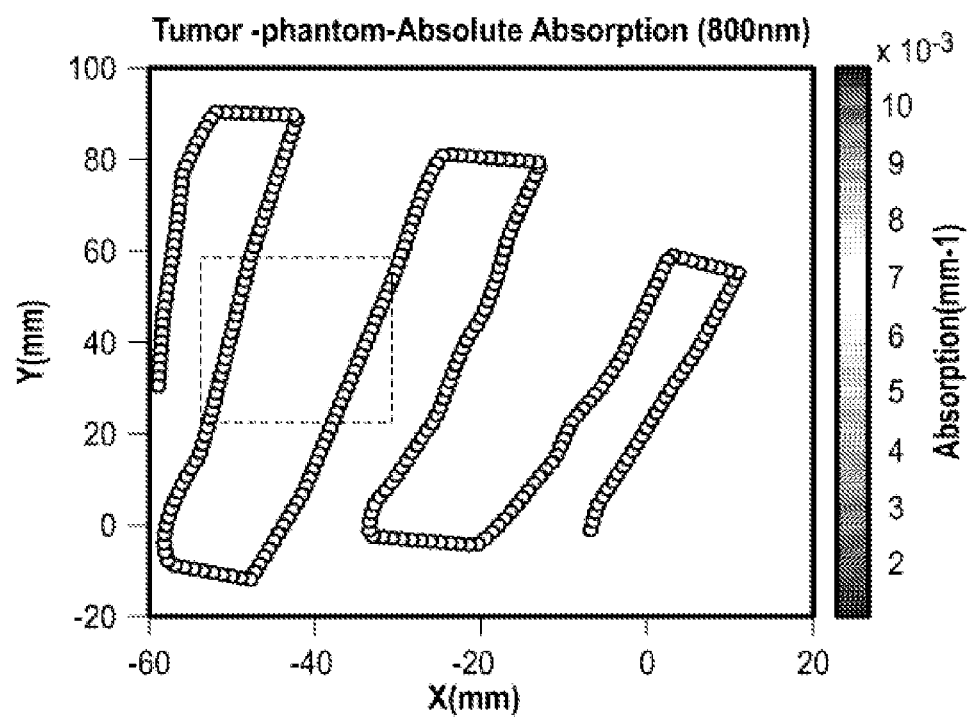
Figure 34:
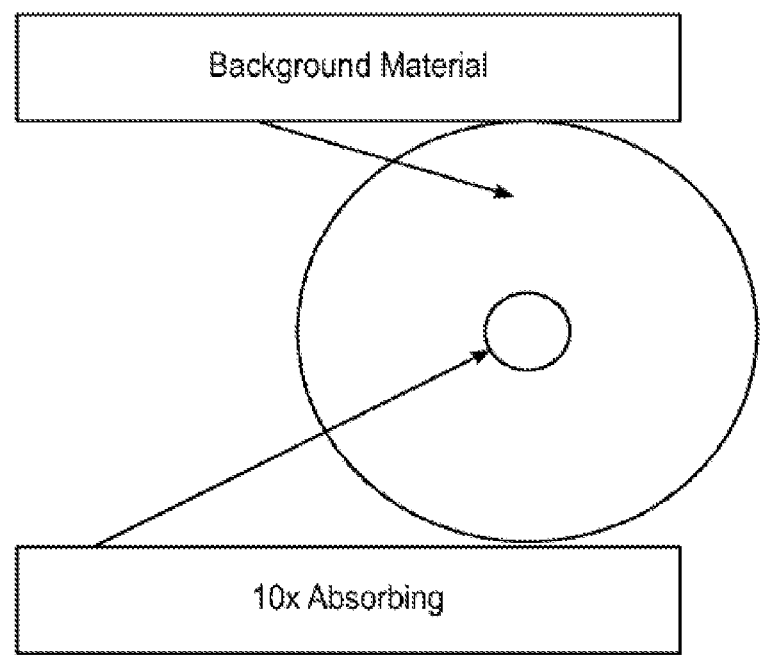
Figure 34:
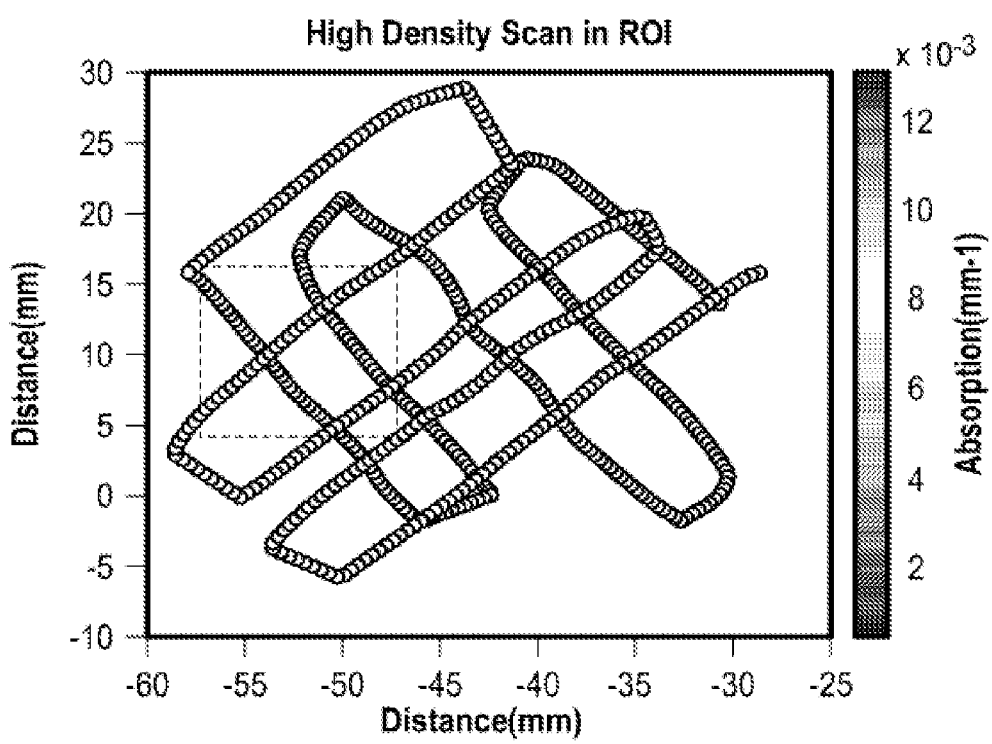

One of the main purposes of the motion tracking system is to improve the speed of the clinical measurements, this section shows some data comparisons between the previous imaging system and the combined fast CW imaging with tracking. The buried tumor simulating phantom was used to compare optical measurements between optical imaging systems. The combined motion/imaging data collected with high-speed CW system and integrated motion tracker was compared to an image taken with the standard FDPM DOSI imaging system that collects data at discrete grid points. FIG. 34 shows a map of absorption values using the standard Broadband Spectroscopy/FDPM DOSI imaging system. The grid was taken with points at 1 cm separation in both directions for a total of 49 measurement locations in 5 minutes. In FIG. 34, the same phantom was imaged using the fast CW imaging system with 400-500 measurements in 12 seconds. The region of interest, shown in the dashed square of FIG. 34, can be reimaged using a higher density of points to further examine spatial sensitivity to the changes in absorption.

Figure 35:
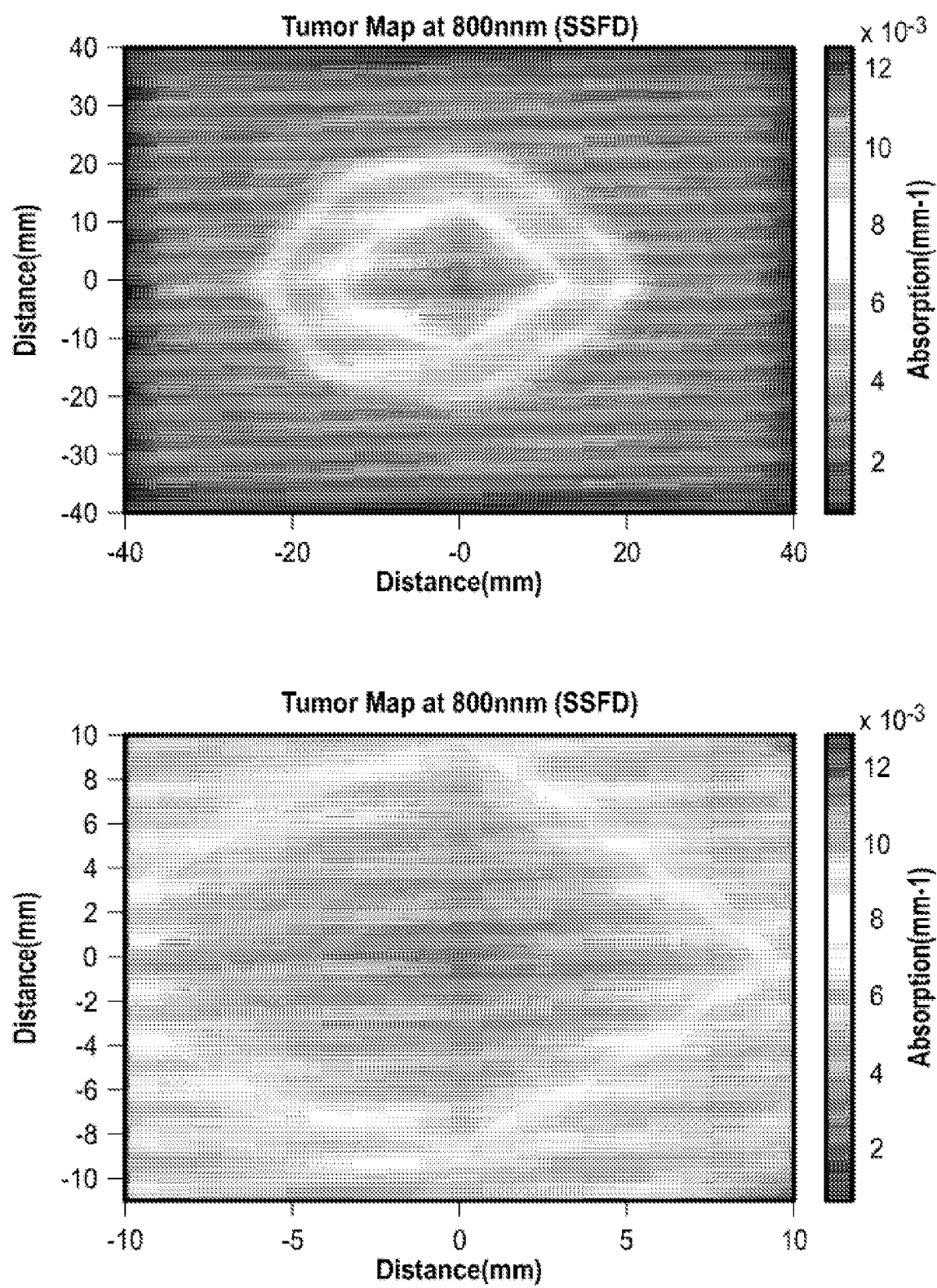
FIG. 35 depicts, in accordance with embodiments herein, interpolated maps of absorption data of buried tumor phantom.
Figure 35:
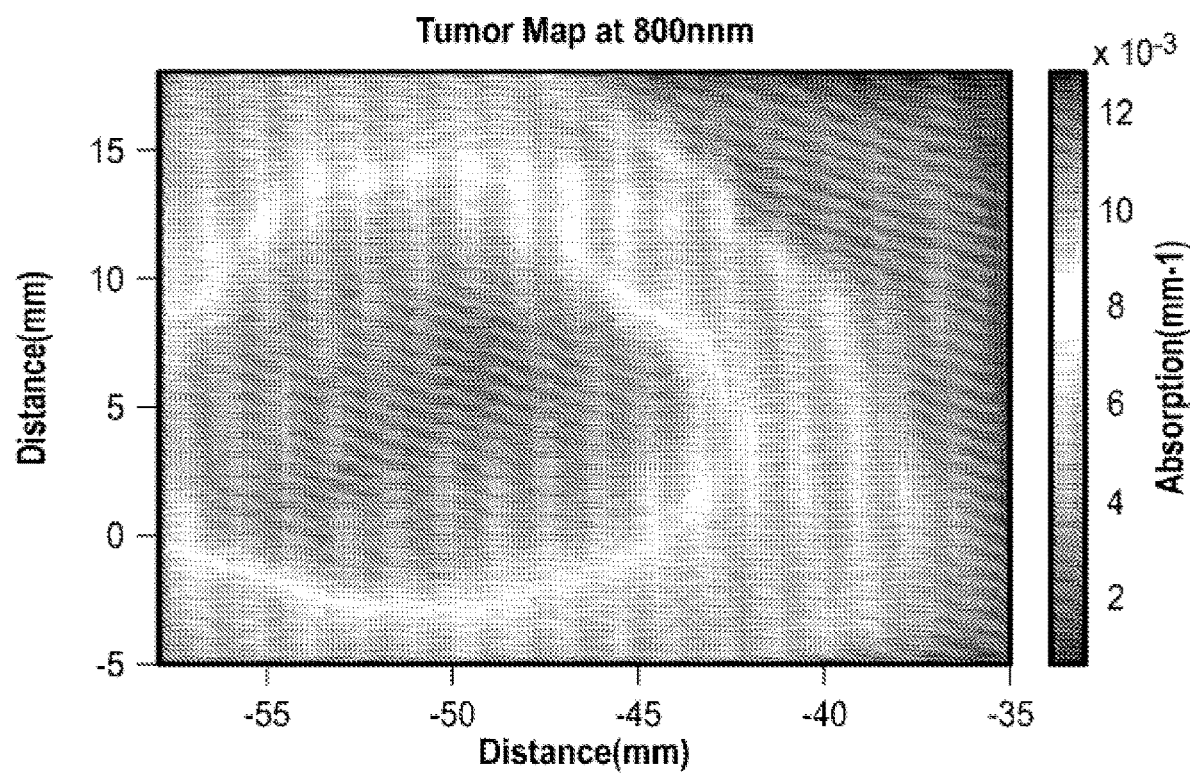

The typical data processing of the FDPM and broadband spectroscopy data taken in a grid usually generates an interpolated image that shows the changes in absorption or chromophore values depending on the application. The interpolated image created from FIG. 34 is shown in the FIG. 35. A zoomed in version of that interpolated image is also shown in FIG. 35, which allows for better comparison to the other measurement data. The interpolated image created using the data from FIG. 34 is shown in FIG. 35.

The higher resolution that is possible by using a motion tracking system better estimates peak contrast values by ensuring that a region of interest is to be scanned with more points. The spatial distribution of optical contrast is of key interest to clinicians in estimating the size of tumor regions, to resolve the smaller optical contrast features, multiple scans are needed of variable spatial scale. A better measure of the true optical contrast gradient can be seen in FIG. 35. The buried tumor phantom has an buried inclusion the shape of a cylinder with sharp gradients along the surface over the edges of the inclusion. The shape of the optical contrast is of interest to physicians and requires several hours to reproduce the results at high enough density with previous FPDM/Broadband Spectroscopy System. The reduction in total measurement time is due to not only being able to measure each location faster, but changing the protocol to first doing a course spatial scale scan, then only measuring regions of interest.

The position data that was used for FIG. 34 and FIG. 35 were based solely on displacement and orientation measurements from the Arduino and were without a virtual scale factor or orienting the path to the surface. The measurements were used as an example of what kind of improvements can be made to the imaging system with the use of motion tracking. Improvements gained by having higher spatial resolution were dependent on having a system that could accurately record the physical location of a measurement on a surface.

Example 7

Conclusions

In accordance with various embodiments herein, the inventors developed a probe tracking system with three functions: variable spatial resolution, improved measurement speed, and comparable results in 3D. The three functions are achievable with this system as long as the accuracy and repeatability can be improved. The goal of variable spatial resolution involves scanning over a large area with a coarse path that shows large features and identifies areas that may need finer scanning. It has been shown that one can refine scans to improve the spatial resolution of the changes that can be measured. This can be seen in the buried tumor phantom results which show the increased resolution measurements taken in a shorter amount of time. The improved measurement speed is primarily derived from the technology development of the fast CW imaging system but the full utilization of that technology was not possible without the recognition of the physical location of measurement. Even without the improved imaging system, removing the alignment step in the breast cancer imaging protocol will reduce the amount of time an appointment lasts. With the combination of the tracking and fast imaging systems, that breast measurements that currently takes between 45-90 minutes could be done in as little as 10-20 minutes. The last goal of comparing data in 3D is something that is being addressed with the data provided from this system. Another advantage of the embodiments disclosed herein is the ability to accurately reconstruct three dimensional optical property distributions only using a handheld probe. Using available inverse modeling software such as NIR-FAST, reconstructions that were only possible with more complex imaging system would be possible using DOSI. Combining the 3D geometry with the location of many measurements allows for the accurate quantification of chromophores in three dimensions. Comparing the 3D distribution of chromophore concentrations allows for more accurate monitoring of metabolism tumor as well as comparison with other 3D modalities such as MRI.

The accuracy calculations ranged from predicted error on a flat surface of 33.3% and 56.3% to the exercise ball with 21.9% and 23.2% and the lower leg with 59.2% and 43%. The main areas of errors come in four distinct categories, Depth Registration, Texture Application, Sensor Measurement, and Virtual Errors.

Depth registration errors were due to noise in the depth measurement that does not reflect the actual surface that is being measured. The Kinect system that was used integrated the depth data as the Kinect is moved to smooth out the surface. One possible problem with this integration is that when the data is not properly aligned, integrating over the whole period can make cumulative errors. One way to address this error was to scan the same structure multiple times to reduce the noise level and possibly change the integration weight to apply a smoothing function during integration. Texture errors can occur when the texture of the image does not properly represent the texture of the 3D model; this can occur with various degrees of error when the texture image and the pose of the Kinect are in slight disagreement with the depth data. This type of error was fixed by using an edge detection scheme or specific fidicual marker that had a particular geometric shape so that the depth scan can be aligned exactly to the texture.

Another potential type of error is sensor measurement error. These errors would be giving inconsistent displacement values or orientation measurements. The calibration steps addresses these errors to an extent, but when combined with virtual calibration errors, the errors may propagate. Virtual errors were the last step in the process which involved registering the sensor data with a known path, as well as placing an unknown path onto the surface. The virtual errors are improved by quantifying the repeatability of the scaling and rotation calibration procedures, as well as making sure the path projection has the same procedure with a known and unknown path. Improvements to the robustness of the projection helps account for small errors in the 3D scanning and texturing process.

Example 8

Position Tracking System Technique

The position tracking system illustrated herein consists of four parts: 1) acquisition of the 3D surface profile over the DOS probe was scanned, 2) capturing the motion of the DOS probe while it was translated across the surface, 3) a position calibration and data fusion scheme to co-register the two pieces of information and 4) integrated probe with tracking electronics and optical fibers.

1) 3D Surface Acquisition:

The inventors utilized a Microsoft Kinect for Windows V1 (Microsoft, WA, USA) to first measure the 3D surface profile. The Kinect device captures surface geometry by projecting and imaging the deformation of a spatial pattern of near-infrared points. Kinect Fusion software (Microsoft, WA, USA) digitizes a surface profile by integrating depth information from multiple views into a single 3D mesh while Kinect device is rotated around an object. The voxel resolution and number of voxels was determined to be 512 voxels per meter and the maximum number of voxels given the resolution. These values were determined to produce a smooth mesh of a patient surface while scanning 1-2 meters away from the patient. Using Meshlab software, the unwanted portions of the 3D mesh scan were removed, and the 3D mesh was smoothed using a Poisson surface reconstruction. Finally, color texturing of the surface profile was performed by combining the 3D mesh with a color image using Point Cloud Library. The texturing is important because the fiducial markers on the skin surface allow translation between real world coordinates and virtual coordinates.

2) Motion Tracking Sensors:

In one embodiment, the inventors integrated a motion sensing system with a DOS imaging probe, consisting of three inertial motion sensors and one optical displacement sensor. The inertial motion sensors included an accelerometer (ADXL345, Analog Devices, MA USA), magnetic compass (HMC5883L, Honeywell, NJ, USA), and a gyroscope (ITG-3200, Invensense, CA, USA) integrated onto a single printed circuit board (PCB) (SEN-10724, Sparkfun, CO, USA). These components were selected for their sampling rate (50-100 Hz) and sensitivity to measure accelerations of the handheld imaging probe at ±2 g. The optical displacement sensor (ADNS-9800, Avago CA, USA), designed for a PC gaming optical mouse, was chosen for its high displacement resolution (9800 dots per inch) and fast motion sampling (up to 21 inches per second).

The sensors were interfaced with an Arduino Due microcontroller (Arduino, Italy) to acquire the sensor data and transfer the data to a PC. The inertial motion sensors were used with a modified implementation of an open source sensor fusion algorithm or mathematical approach using a Directional Cosine Matrix to represent changes in orientation of the imaging probe. The optical displacement sensor was placed on the bottom of the imaging probe and measured the displacement of the imaging probe on the skin surface. This displacement, combined with orientation data from the DCM algorithm allows for the calculation of the relative motion along the measurement surface.

Figure 36:
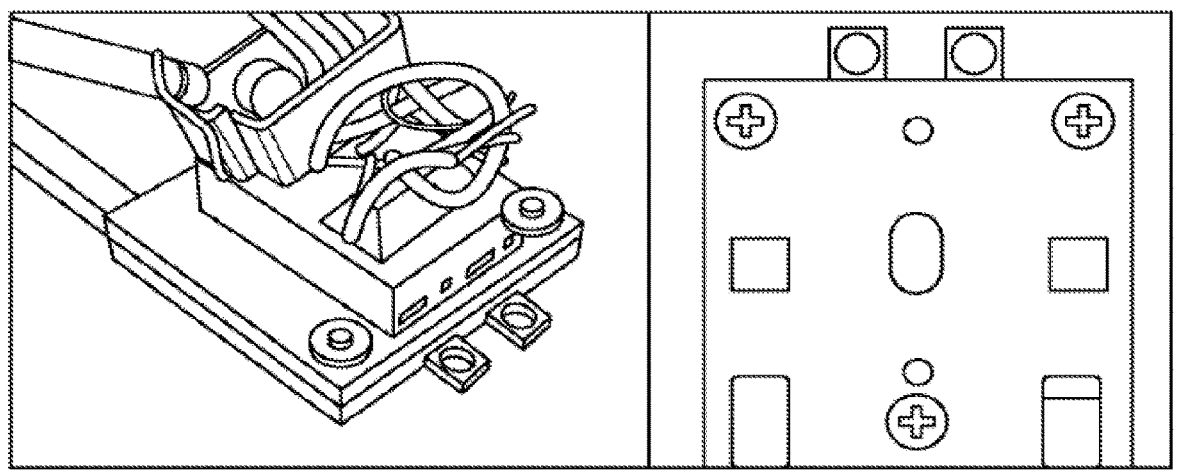
FIG. 36 depicts, in accordance with embodiments herein, one embodiment of the imaging probe. (a) Imaging probe with integrated motion tracking software, two features on top of probe for alignment with fidicual markers. (b) Bottom view of imaging probe showing optical fiber location and source detector separation of 28 mm.

3) Data Fusion:

Virtual mesh was loaded into JMonkeyEngine. The acquisition of data was performed using serial USB. The initial path was recorded to find rotation correction using fiducial markers. Projection algorithm was used for interpolation of data based on estimated location 4) Optical Imaging Integration:

The motion tracking system was integrated with a custom optical imaging probe. The probe combined the motion tracking electronics with optical fibers to acquire optical measurements. The optical measurements were done with a Laser Breast Scanner system. Frequency Domain Photon Migration (FDPM) measurements were acquired without broadband reflectance due to crosstalk between 850 nm VCSEL used in the ADNS9800 chip and the spectrometer. The imaging probe is shown in FIG. 36.

Example 9

System Performance

Figure 37:
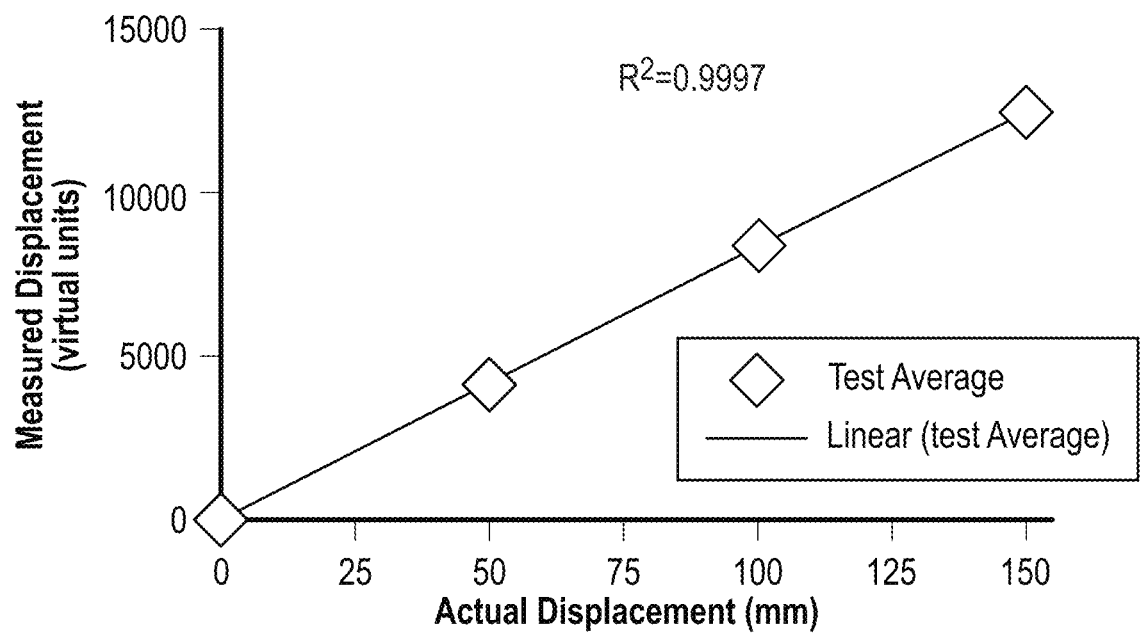
FIG. 37 depicts, in accordance with embodiments herein, the performance and validation of the apparatus disclosed herein on both flat and curved surfaces. (Top) Plot showing measured sensor distances and real distances from forearm recording and linera fit for scale. (Bottom) Recorded path through grid points shown on virtual forearm mesh. Path starting from top right marker
Figure 37:
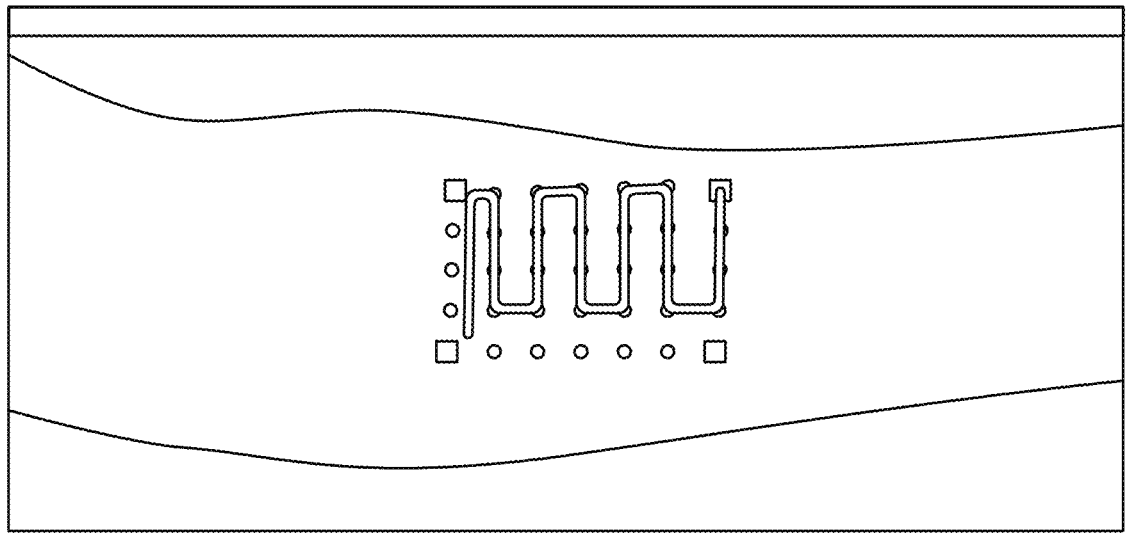

The performance of the system was assessed by the accuracy and precision in which the position was determined. In order to assess the precision of the path recording on human skin, several paths of various lengths were recorded and then repeated. This repetition allowed for the calculation of a scale factor between real displacement and measured sensor units. The linear displacement results are shown in FIG. 37 (top). Error bars are small and therefore not included.

The accuracy of the system was measured by estimating the position of an unknown point on the virtual patient surface and comparing to the measured position on the patient. The full process of 3D scanning a tissue region, selecting fidicual markers, and accounting for rotation correction was performed. Then a path was recorded from a fidicual marker to various grid locations. The recorded path was seen on the virtual surface in FIG. 37 (bottom) and the estimation of accuracy can be seen in Table 8.

TABLE 8

Unknown Point Estimation

| Path Number | Real Path Distance (mm) | Estimated Path Distance (mm) | Final Position Distance (mm) | % Difference |
|---|---|---|---|---|
| 1 to 2 | 17.179 | 16.937 | 0.987 | 5.74% |
| 1 to 3 | 38.461 | 39.878 | 3.834 | 9.97% |
| 1 to 4 | 61.744 | 64.010 | 6.955 | 11.26% |

TABLE 9

Unknown Point Estimation

| Path Number | Real Path Distance (mm) | Estimated Path Distance (mm) | Final Position Distance (mm) | % Difference |
|---|---|---|---|---|
| 1 to 2 | 15.709 | 16.100 | 0.705 | 4.49% |
| 1 to 3 | 29.842 | 23.073 | 6.923 | 23.20% |
| 1 to 4 | 41.994 | 34.771 | 7.373 | 17.56% |

Example 10

Demonstration with DOS Handheld Probe

Figure 38:
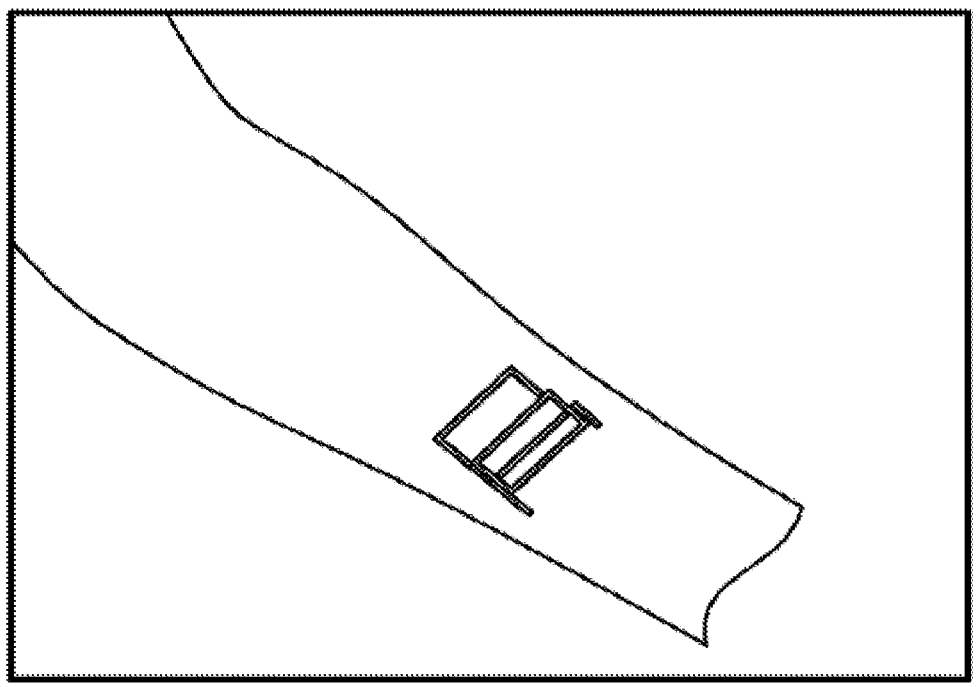
FIG. 38 depicts, in accordance with embodiments herein, a demonstration of the tracker system while collecting DOS data
Figure 38:
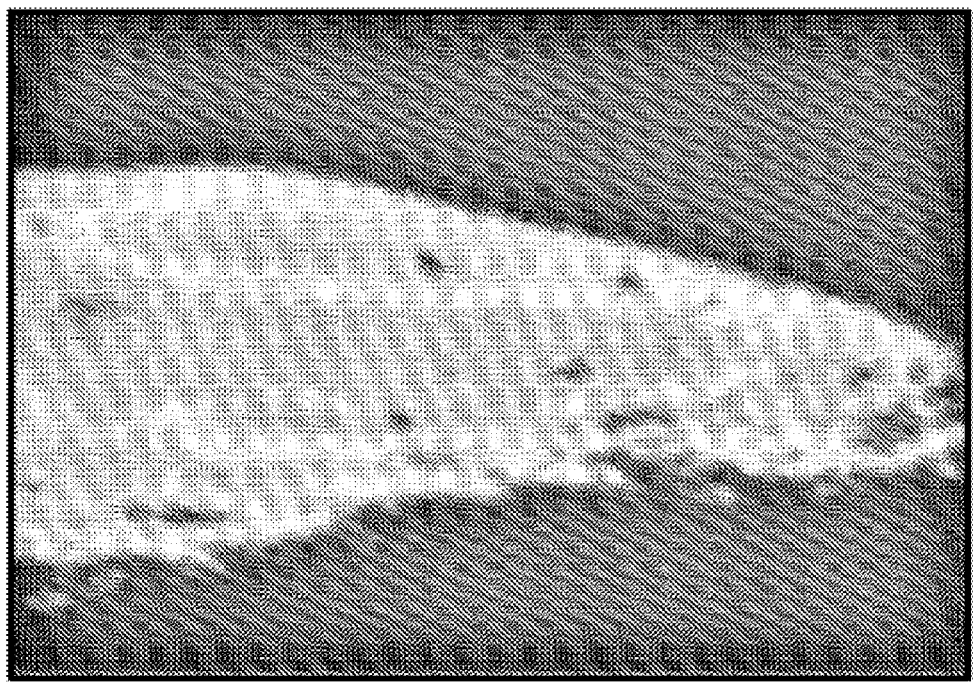
Figure 38:
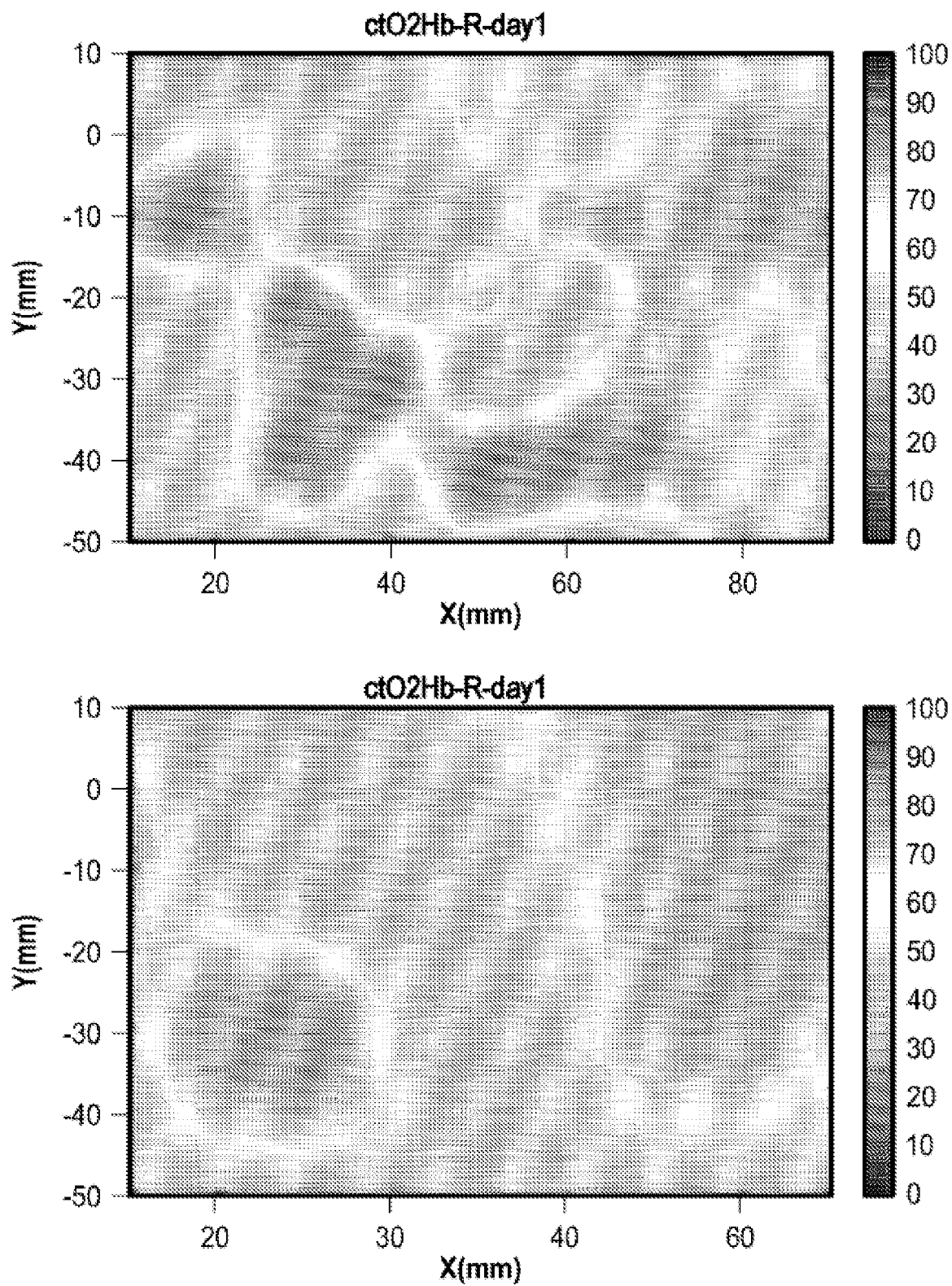

In one embodiment the position tracking was used to create high resolution images of optical property as well as chromophore distribution. FIG. 38 illustrates a demonstration of the tracker system while collecting DOS data Example 11

Advantages

The two main advantages of the position tracking system are the ability to recreate and compare measurements between multiple patient measurements as well as remove the need for the time consuming anatomical landmark based grid system. One important innovation that the motion tracking system allows is the accurate visualization of the optical measurements in patient specific 3D geometry.

The results of the accuracy tests indicate a relatively consistent output that may need slight rotation correction. The relationship between longer recorded paths and more error between estimated points can indicate that a small rotation may reduce the point errors. The results of measuring the forearm with three different methods seems to provide agreement and show that using higher resolution measurements at non fixed spatial resolution can be comparable to wide field imaging techniques such as SFDI. The depth sensitivity could be increased using a longer source detector separation on the imaging probe, but for the best comparison 28 mm was used to provide depth sensitivity around 14 mm. The main findings of the comparison is that the grid is able to locate features such as arteries but in areas with deeper or smaller arteries or landmarks, non-fixed spatial resolution is able to more accurate show contrast.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An apparatus for tracking a 3D surface profile of a subject, comprising:
  one or more motion tracking sensors integrated/ with an imaging probe, comprising
  one or more motion tracking sensors first captures a 3D surface profile that records the location of one or more measurement points by co-registering them with one or more anatomical landmarks of the subject,
  wherein the one or more motion tracking sensors are operably connected to a microcontroller,
  wherein the microcontroller receives and stores 3D surface profile data from the one or more motion tracking sensors, and
  second the imaging probe is placed as part of a diffuse optical spectroscopy (DOS) sensing technique of the subject,
  wherein the captured 3D surface profile provides increased accuracy and decreased measurement time for the DOS sensing technique, and wherein the apparatus is directed to map out external and deformable body structures.

2. The apparatus of claim 1, wherein the one or more motion tracking sensors comprise an inertial motion sensor and an optical displacement sensor.

3. The apparatus of claim 1, wherein the imaging probe is an electronic imaging probe.

4. The apparatus of claim 1, wherein the imaging probe is a handheld imaging probe.

5. The apparatus of claim 1, wherein the apparatus further acquires optical data.

6. An apparatus, comprising:
   one or more motion tracking sensors compromising an accelerometer, a gyroscope, a magnetic compass, and an optical displacement sensor,
   wherein the one or more motion tracking sensors are operably connected to a microcontroller and a handheld imaging probe,
   wherein the microcontroller receives and stores 3D surface profile data from the one or more motion tracking sensors, and
   wherein first the 3D surface profile records a plurality of measurement points by co-registering them with one or more anatomical landmarks of a subject, and
   wherein second a probe is placed on the subject as part of a diffuse optical spectroscopy (DOS) sensing technique, and
   wherein third the plurality of measurement points are processed to improve accuracy and measurement time of the DOS sensing technique, and
   wherein the apparatus is directed to map out external and deformable body structures.

7. The apparatus of claim 6, wherein the apparatus further comprises visualization of imaging data.

8. The apparatus of claim 6, wherein an user of the apparatus can dynamically adjust the data collection field such as to collect higher spatial resolution data over a region of interest without having to separately record the additional sampling points.

9. The apparatus of claim 6, wherein the apparatus operates automatically or semi-automatically.

10. The apparatus of claim 6, wherein the automated tracking apparatus improves the usability of the device and reduces the complexity of DOS and other imaging probe-based techniques.

11. A device comprising:
   one or more sensors that record relative motion information from handheld electronics, and a 3D scan, using software to record and visualize position and information about surface,
   wherein the one or more sensors comprises an accelerometer, a gyroscope, a magnetic compass, and an optical displacement sensor,
   wherein the one or more sensors are operably connected to a microcontroller and the handheld electronic, and
   wherein the microcontroller receives and stores 3D surface profile data from the one or more sensors, and transfers the 3D surface profile data to a computer for recording and visualizing position and information about surface, and
   wherein the device operates by the following steps: first the 3D surface profile records a plurality of measurement points by co-registering them with one or more anatomical landmarks of a subject, second a probe is placed on the subject as part of a diffuse optical spectroscopy (DOS) sensing technique, and third the plurality of measurement points are processed to improve accuracy and measurement time of the DOS sensing technique, and
   wherein the device is directed to map out external and deformable body structures.

* * * * *